(12) United States Patent
Otvos

(10) Patent No.: US 7,790,465 B2
(45) Date of Patent: Sep. 7, 2010

(54) METHODS, SYSTEMS AND COMPUTER PROGRAMS FOR ASSESSING CHD RISK USING ADJUSTED LDL PARTICLE NUMBER MEASUREMENTS

(75) Inventor: James D. Otvos, Apex, NC (US)

(73) Assignee: LipoScience, Inc., Raleigh, NC (US)

( * ) Notice: Subject to any disclaimer, the term of this patent is extended or adjusted under 35 U.S.C. 154(b) by 1176 days.

(21) Appl. No.: 11/379,275

(22) Filed: Apr. 19, 2006

(65) Prior Publication Data

US 2006/0183234 A1  Aug. 17, 2006

Related U.S. Application Data

(63) Continuation-in-part of application No. PCT/US2004/034906, filed on Oct. 21, 2004.

(60) Provisional application No. 60/513,795, filed on Oct. 23, 2003.

(51) Int. Cl.
  *G01N 33/92* (2006.01)
  *G06F 19/00* (2006.01)

(52) U.S. Cl. .............................. 436/71; 436/63; 436/86; 436/173; 702/19; 702/22; 702/23; 702/32

(58) Field of Classification Search ................. 436/63, 436/71, 86, 173; 702/19, 22, 23, 26, 29, 702/32
See application file for complete search history.

(56) References Cited

U.S. PATENT DOCUMENTS

| 4,933,844 | A | 6/1990 | Otvos |
| 5,343,389 | A | 8/1994 | Otvos |
| 6,576,471 | B2 | 6/2003 | Otvos |
| 6,617,167 | B2 | 9/2003 | Otvos et al. |
| 6,653,140 | B2 * | 11/2003 | Otvos ........................ 436/71 |
| 6,812,033 | B2 * | 11/2004 | Shewmake et al. ............ 436/71 |
| 7,243,030 | B2 * | 7/2007 | Reeve et al. ................... 702/19 |
| 2003/0235918 | A1 * | 12/2003 | Shewmake et al. ............ 436/13 |
| 2004/0098208 | A1 | 5/2004 | Reeve et al. |
| 2004/0142496 | A1 * | 7/2004 | Nicholson et al. ........... 436/536 |
| 2005/0042761 | A1 * | 2/2005 | Shewmake et al. ............ 436/71 |
| 2008/0038829 | A1 * | 2/2008 | Kremer et al. ................ 436/71 |
| 2008/0121025 | A1 * | 5/2008 | Okazaki .................... 73/61.52 |

FOREIGN PATENT DOCUMENTS

| WO | WO 93/03450 | 2/1993 |
| WO | WO 00/51054 | 8/2000 |
| WO | WO 2005/043171 A1 | 5/2005 |
| WO | WO 2005/119285 A1 | 12/2005 |

OTHER PUBLICATIONS

National Cholesterol Education Program,; "Detection, Evaluation, and Treatment of High Blood Cholesterol in Adults, Adult Treatment Panel II" *Circulation* 89:3 1329-1445 (1994).

(Continued)

*Primary Examiner*—Maureen M Wallenhorst
(74) *Attorney, Agent, or Firm*—Myers Bigel Sibley & Sajovec, P.A.

(57) ABSTRACT

Methods, computer program products and apparatus determine a subject's risk of having or developing CHD using a calculated LDL particle risk number and/or a mathematical model of risk associated with LDL particles that adjusts concentrations of at least one of small and large LDL particle measurements to reflect predicted CHD risk.

38 Claims, 9 Drawing Sheets

OTHER PUBLICATIONS

Cromwell et al.; "Low-density lipoprotein particle number and risk for cardiovascular disease" *Curr. Atheroscler. Rep.* 6 381-387 (2004).

Campos et al.; "LDL Particle Size Distribution" *Arteriosclerosis and Thrombosis* 12:12 1410-1419 (1992).

Campos et al.; "Predominance of large LDL and reduced HDL2 cholesterol in normolipidemic men with coronary heart disease" *Arterioscler Thromb Vasc Biol* 15 1043-1048 (1995).

Campos et al.; "Low-density lipoprotein size, pravastatin treatment, and coronary events" *JAMA* 286 1468-1474 (2001).

Dreon et al.; "Change in dietary saturated fat intake is correlated with change in mass of large low-density-lipoprotein particles in men" *Am. J. Clin. Nutr.* 67 828-836 (1998).

Freedman et al.; "Relation of Lipoprotein Subclasses as Measured by Proton Nuclear Magnetic Resonance Spectroscopy to Coronary Artery Disease" *NMR-Determined Lipoprotein subclasses and CAD* 1046-1053. Arteriosclerosis, Thrombosis & Vascular Biology, 1998.

Griffin et al; "Role of plasma triglyceride in the regulation of plasma low density lipoprotein (LDL) subfractions: relative contribution of small, dense LDL to coronary heart disease risk" *Atherosclerosis* 106 241-253 (1994).

Grundy, S.M. et al.; "Hepatic lipase influences high density lipoprotein subclass distribution in normotriglyceridemic men: genetic and pharmacological evidence" *J. Lipid Res.* 40 229-234 (1999).

Hildebrand, F.B.; *Introduction to Numerical Analysis*, $2^{nd}$ edition 314-326, 539-567, McGraw-Hill (1975).

Krauss; "Relationship of intermediate and low-density lipoprotein subspecies to risk of coronary artery disease" *American Heart Journal* 113:2, Part 2 578-582 (1987).

McNamara Jr., et al.; "Differences in LDL subspecies involve alterations in lipid composition and conformational changes in apolipoprotein B" *J. Lipid Res.* 37 1924-1935 (1996).

Mierisová et al.; "MR spectroscopy quantitation: a review of frequency domain methods" *NMR Biomed.*, 2001.

Mora et al.; "Both Large and Small LDL Particle concentrations are Independently Associated with Carotid Atherosclerosis in the Multi-Ethnic Study of Atherosclerosis (MESA)" 2005 Scientific Sessions of the American Heart Association, Dallas, Texas *Circulation* 112 II-802 (2005). Abstract only.

Mora, et al.; Lipids, Lipoprotein Subclasses, and Carotid Atherosclerosis in the Multi-Ethnic Study of Atherosclerosis (MESA)—Submitted for publication as part of oral presentation at the $78^{th}$ Annual Scientific Sessions of the American Heart Association 2-28 (2005).

O'Leary et al.; "Intima-media thickness; a tool for atherosclerosis imaging and event prediction" *Am. J. Cardiol.* 90 18L-21L (2002).

Otvos, J.D. et al.; "Development of a proton nuclear magnetic resonance spectroscopic method for determining plasma lipoprotein concentrations and subspecies distributions from a single, rapid measurement" *Clin. Chem.* 38 1632-1638 (1992).

Otvos, J.D. et al.; "Measurement of lipoprotein subclass profiles by nuclear magnetic resonance spectroscopy" *Clin. Lab.* 48 171-180 (2002).

Otvos et al.; "Low-Density Lipoprotein and High-Density Lipoprotein Particle Subclasses Predict Coronary Events and Are Favorably Changed by Gemfibrozil Therapy in the Veterans Affairs High-Density Lipoprotein Intervention Trial" *Circulation* 113 1556-1563 (2006).

Patsch et al.; "Characterization of lipoprotein in a kindred with familial hypercholesterolemia" *J. Lipid Res.* 23 1196-1205 (1982).

Rapp et al.; "Particle size distribution of lipoproteins from human atherosclerotic plaque: A preliminary report" *Journal of Vascular Surgery* 9:1 81-88 (1989).

Redgrave, TG et al.; "Changes in plasma very low density and low density lipoprotein content, composition, and size after a fatty meal in normo- and hypertriglyceridemic man" *J. Lipid Res.* 20 217-29 (1979).

Rifai, N. et al.; *Handbook of LipoProtein Testing*, $2^{nd}$ Edition, Washington, DC, AACC Press; 2000, 609-623.

Rosenson et al.; Relations of lipoprotein subclass levels and low density lipoprotein size to progression of coronary artery disease in the Pravastatin Limitation of Atherosclerosis in the Coronary Arteries (PLAC-1) trial *Am. J. Cardio.* 90 89-94 (2002).

Rumsey et al.; "Cryopreservation with sucrose maintains normal physical and bioloOgical properties of human plasma low density lipoproteins" *J. Lipid. Res.* 33 1551-1561 (1992).

Sacks et al.; "Clinical review 163: Cardiovascular endocrinology: Low density lipoprotein size and cardiovascular disease: a reappraisal" *J. Clin. Endocrinol Metab.* 88 4525-4532 (2003).

Wilson et al.; "Impact of National Guidelines for Cholesterol Risk Factor Screening" *JAMA* 262:1 41-44 (1989).

Wilson et al.; "Prediction of Coronary Heart Disease Using Risk Factor Categories" *Special Report from the Framingham Heart Study, National Heart, Lung and Blood Institute*, Framingham, Mass. 1837-1847, Circulation, vol. 97, 1998, pp. 1837-1847.

News Release/NC State University "New Test More Accurately Measures Risk of Heart Disease, Study Finds" 6 pp (1998) XP-002139898.

"Magnetic Resonance Test May Give Better Assessment of Heart Disease Risk" URL:<http://www.plsgroup.com/dg/8DE5A.htm> (1998) XP-002139896.

"Company Profile: Lipomed Technology Anticipated to be a Leading Predictor of Heart Disease" 2 pp (1998) XP-002139897.

International Search Report for PCT/US2004/034906; Date of mailing Apr. 5, 2005.

* cited by examiner

| PATIENT NAME | | SEX | AGE | CLINICIAN | |
|---|---|---|---|---|---|
| | | | | | |

| | | | CLIENT NAME AND ADDRESS |
|---|---|---|---|
| PATIENT ID | BIRTH DATE | ACCESSION # | |
| | | | |

| DATE COLLECTED | DATE RECEIVED | REPORT DATE AND TIME | REQUISITION NUMBER | COMMENT |
|---|---|---|---|---|
| | | | | |

LDL-BASED RISK

| | nmol/L | OPTIMAL | NEAR OPTIMAL | BORDERLINE-HIGH | HIGH | VERY HIGH |
|---|---|---|---|---|---|---|
| RISK$_{LDL}$ | 2400 | <1000 | 1000 - 1399 | 1400 - 1799 | 1800 - 2200 | >2200 |

| | nmol/L | LOW | MODERATE | BORDERLINE | HIGH |
|---|---|---|---|---|---|
| LARGE LDL-P | 1200 | <300 | 300-499 | 500-800 | >800 |

| | nmol/L | LOW | MODERATE | BORDERLINE | HIGH |
|---|---|---|---|---|---|
| SMALL LDL-P | 600 | <500 | 500-849 | 850 - 1200 | >1200 |

LIPIDS

| | mg/dL | | mg/dL |
|---|---|---|---|
| TOTAL CHOLESTEROL | 234 | LDL CHOLESTEROL | 161 |
| | DESIRABLE <200 | | DESIRABLE <130 |
| HDL CHOLESTEROL | 37 | TRIGLYCERIDES | 181 |
| | DESIRABLE >40 | | DESIRABLE <150 |

*FIG. 3*

METHODS, SYSTEMS AND COMPUTER PROGRAMS FOR ASSESSING CHD RISK USING ADJUSTED LDL PARTICLE NUMBER MEASUREMENTS

RELATED APPLICATION

This application is a continuation-in-part of PCT Application Serial No. US/2004/034906, filed Oct. 21, 2004, which claims priority to U.S. Provisional Patent Application Ser. No. 60/513,795, filed Oct. 23, 2003, the contents of which are hereby incorporated by reference as if recited in full herein.

FIELD OF THE INVENTION

The present invention relates generally to analysis of lipoproteins. The invention may be particularly suitable for NMR analysis of lipoprotein constituents in blood plasma and serum.

BACKGROUND OF THE INVENTION

In the past, "advanced" lipoprotein test panels have typically included a lipoprotein measurement of average low-density lipoprotein (LDL) particle size as well as LDL particle number, the latter representing the concentration or quantity (in concentration units such as nmol/L) and the former representing the average size of the LDL particles (in nm units) making up the LDL in the sample. For example, in the NMR LipoProfile® lipoprotein panel report available from LipoScience, Inc., located in Raleigh, N.C., the average LDL particle size corresponds to the average size of a sample's total LDL particles, i.e., the average size of the combined small, intermediate and large LDL particles. Any one person can have LDL particles present in a continuum of different particle sizes. See www.liposcience.com and U.S. Pat. No. 6,576,471 for exemplary reports of particular lipoprotein subclass parameters, the contents of the patent are hereby incorporated by reference as if recited in full herein.

Generally stated, U.S. Pat. No. 4,933,844, entitled Measurement of Blood Lipoprotein Constituents by Analysis of Data Analysis of Data Acquired from an NMR Spectrometer to Otvos and U.S. Pat. No. 5,343,389, entitled Method and Apparatus for Measuring Classes and Subclasses of Lipoproteins, also to Otvos, describe NMR evaluation techniques that concurrently obtain and measure a plurality of different lipoprotein constituents in an in vitro blood plasma or serum sample. See also, U.S. Pat. No. 6,617,167, entitled Method Of Determining Presence And Concentration Of Lipoprotein X In Blood Plasma And Serum. The contents of all the above patents are hereby incorporated by reference as if recited in full herein. To evaluate the lipoproteins in a blood plasma and/or serum sample, the amplitudes of a plurality of NMR spectroscopy derived signals within a chemical shift region of the NMR spectrum are derived by deconvolution of the composite signal or spectrum and are compared to predetermined test criteria to evaluate a patient's risk of having or developing coronary artery or heart disease.

Referring to FIG. 1, it is noted that the constituents of certain subclasses of lipoproteins have overlapping signals. For example, LDL constituent values, shown for clarity as only two (L2 and L5) LDL subclass constituent values, when presented on a spectrum graph of signal intensity versus ppm, can overlap considerably. The overlapping nature of the signals can produce a regression matrix that is nearly singular. Conventional statistical evaluation methods that employ non-negative least squares techniques on nearly collinear data may have unstable and variable regression coefficients. See Myers, Raymond H., *Classical and Modern Regression with Applications*, (2d ed., Mass. PWS-Kent, 1990); Box et al., *Statistics for Experimenters; An Introduction to Design, Data Analysis, and Model Building*, (New York, Wiley, 1978).

More recently, sample evaluation methodologies have been developed which can provide increased resolution and/or increased reliability in measurements of discrete size segments or size categories of lipoprotein subclass parameters of interest, such as LDL subclass particle concentrations in a biosample of interest. See, e.g., U.S. patent application Ser. No. 10/691,103, entitled Methods, Systems and Computer Programs for Deconvolving the Spectral Contribution of Chemical Constituents With Overlapping Signals, the contents of which are hereby incorporated by reference as if recited in full herein.

While average LDL particle size and/or total LDL particle number can provide clinically useful information and successfully identify persons that are at risk for coronary heart disease (CHD) and/or coronary artery disease (CAD), this information may discount or suppress the actual predictive risk in some samples for some people. Further, measuring the content of LDL in an in vitro blood plasma or serum sample may not be representative of a person's true risk. In view of the foregoing, there remains a need to provide improved predictive models for assessing a person's risk of developing or having CHD.

SUMMARY

Certain embodiments of the present invention are directed at providing methods, systems, and computer program products with at least one adjusted measure of LDL particles of a discrete size range taken from a blood plasma or serum sample that may provide a better and/or easier to understand risk number to facilitate patient risk stratification and enable more effective treatment decisions compared with use of conventional markers of LDL-based risk, such as LDL cholesterol. The adjusted measures may employ a mathematical model that can improve and/or increase the predictive power of a CHD risk analysis over a population. The predictive risk assessment number and/or models may be particularly useful for both automated screening for CHD risk and making more effective therapeutic management decisions to lower the risk of the patient for CHD.

Embodiments of the present invention provide a LDL risk number (i.e., a weighted concentration of LDL particles or a weighted LDL particle number) that can be easily reviewed by a clinician to assess whether therapy is indicated and/or to track efficacy of a therapy (whether physical and/or medications, such as statins). The LDL risk number can be identified as a weighted LDL parameter that in some embodiments can be referred to as a "$\text{Risk}_{LDL}$", "wLDL-P" or a "R-LDL-P" number on a lab report to identify the test parameter as being an LDL risk predictor from LipoScience, Inc., located in Raleigh, N.C., as presently contemplated by embodiments of the present invention.

Some embodiments are directed to methods of determining a subject's risk of having and/or developing CHD. The methods include: (a) obtaining concentration measurements of both small and large LDL subclass particles in a blood plasma or serum sample; (b) programmatically adjusting at least one of the small and large LDL subclass particle measurement numbers; and (c) determining a subject's risk of having and/or developing CHD based on the adjusted small and/or large LDL subclass particle measurement numbers.

The adjusting can be based on a predetermined mathematical model that predicts a subject's LDL-based risk. The mathematical models may be configured to adjust the measured small and large LDL subclass particle concentration values in plasma and/or serum. The predictive mathematical models can be configured to define a single predictive number or variable that can be used to identify those patients that may qualify for therapy and to track therapies for efficacy (i.e. the predictor variable is a sensitive measure of the risk associated with a particular make-up of LDL particles in a patient and is able to show a reduction in the value of the predictor variable upon successful therapeutic intervention).

In certain embodiments, a predetermined mathematical LDL risk model is configured to evaluate each measured amount of predetermined ranges of LDL subclass particles, then automatically calculate a weighted LDL particle risk number for a particular sample/person considering the amount of each predetermined LDL particle subclass. Embodiments of the invention can analyze samples to provide discrete measurements for at least small LDL particles and large LDL particles, recognizing that each size category can have a different degree of atherogenicity, and then calculate a LDL predictor variable considering each predetermined subclass particle measurement. That is, a sample that has a high concentration (high particle number) of large LDL subclass particles can be indicative of increased risk as well as a sample that has a high concentration of small LDL subclass particles. The model can distinguish risks for two people with the same total number of LDL particles, as the risk may differ if one person has more small and fewer large LDL subclass particles than the other.

In particular embodiments, the LDL particle number risk predictor variable ($R_{LDL}$) can be calculated by assigning a first weighted value to the amount of small LDL subclass particles ($LDL_S$) and a second different weight to the amount of large LDL subclass particles ($LDL_L$) measured in the sample. The weighting can be carried out so that the concentration of the $LDL_L$ particles is increased relative to the small $LDL_S$.

The predictive mathematical (LDL subclass risk) model can be used with NMR signal measurement methods that measure lipoprotein constituents using signals having spectral contribution from chemical constituents having overlapping signals. In certain embodiments, the LDL subclass size ranges may be further defined as three, or even more, different discrete and measurable components (i.e., L1, L2, L3, L4) and each individually weighted according to the predetermined mathematical model.

Other embodiments are directed to methods of determining a subjects risk of having and/or developing CHD. The methods include: (a) measuring concentrations of small and large LDL subclass particles in an in vitro blood plasma and/or serum sample of interest; and (b) electronically adjusting at least one of the small or large LDL subclass particle concentration measurements based on a predetermined mathematical model to thereby determine a subject's LDL-based risk of CHD.

Still other methods include: (a) obtaining NMR-derived concentration measurements of small and large LDL subclass particles in a biosample of interest; (b) applying a weighting factor to at least one of the measured small LDL particle and large LDL particle concentrations; and (c) calculating a LDL risk predictor number using the weighted LDL particle concentration.

The LDL risk predictor number may be a weighted LDL particle number that is unitless or expressed in units of concentration (such as, for example, mmol/L).

Some embodiments are directed to computer program products for adjusting in vitro concentrations of LDL particles. The computer program products include a computer readable storage medium having computer readable program code embodied in the medium. The computer-readable program code includes: (a) computer readable program code configured to adjust measured in vitro concentrations of at least one of small and large LDL particle subclasses to generate a LDL risk number to reflect a subject's risk of having or developing CHD.

Additional embodiments are directed to apparatus for obtaining data regarding lipoprotein constituents in a subject. The apparatus includes: (a) an NMR spectrometer for acquiring at least one NMR spectrum of an in vitro blood plasma or serum sample; and (b) a controller. The controller includes: (a) computer program code for determining concentrations of small and large LDL particle subclasses in the sample undergoing analysis; and (b) computer program code for adjusting at least one of the determined small and large LDL particle concentrations to reflect a risk of developing or having CHD.

Other embodiments are directed to methods of evaluating a person's risk of CHD. The methods include: calculating a weighted LDL lipoprotein risk parameter number using in vitro concentration measurements of at least two different sizes of a patients LDL particles, wherein at least one of the concentration values is increased relative to the measured small LDL particle concentration.

The methods may also include defining a risk of CUD associated with the weighted LDL risk parameter number. The methods can include adjusting an IDL particle measurement and combining the adjusted IDL particle measurement with the small and large LDL concentrations to generate the LDL risk number.

As will be appreciated by those of skill in the art in light of the present disclosure, embodiments of the present invention may include methods, systems, apparatus and/or computer program products or combinations thereof.

The foregoing and other objects and aspects of the present invention are explained in detail in the specification set forth below.

BRIEF DESCRIPTION OF THE FIGURES

FIG. 3 is an exemplary report that uses a LDL Risk number to reflect a subject's LDL-based risk according to embodiments of the present invention.

DETAILED DESCRIPTION OF EMBODIMENTS OF THE INVENTION

Figure 1:
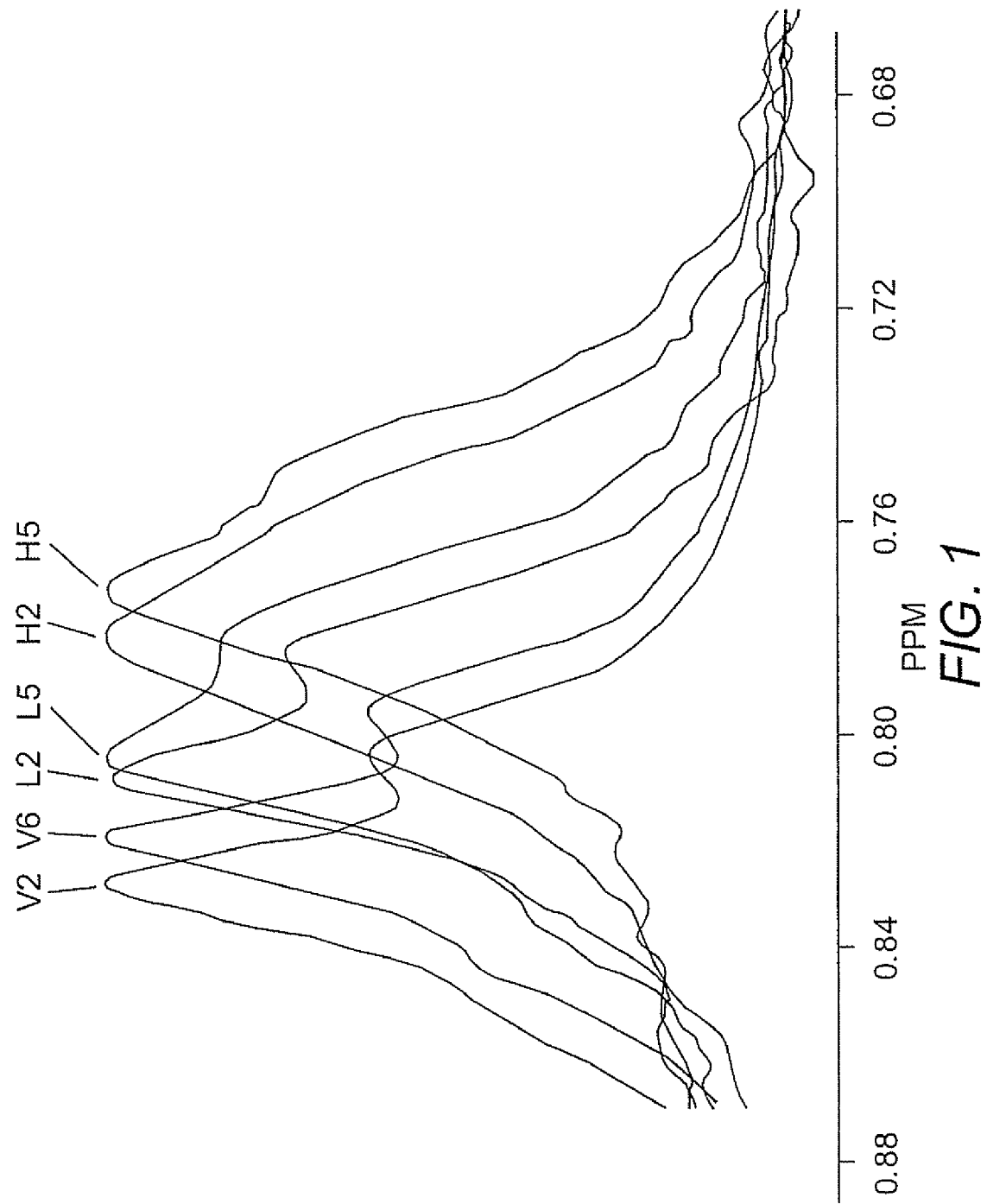
FIG. 1 is a graph showing the chemical shift spectra of a representative sample of lipoprotein constituent subclasses.

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

The term "programmatically" means carried out using computer program directed operations. The terms "automated" and "automatic" means that the operations can be carried out with minimal or no manual labor or input. The term "semi-automated" refers to allowing operators some input or activation, but the calculations and signal acquisition as well as the calculation of the concentrations of the ionized constituent(s) is done electronically, typically programmatically, without requiring manual input.

Presently, the LDL particle sizes are characterized as Pattern A (large) and Pattern B (small). Pattern A can be defined as large average particle sizes which typically includes sizes of between about 20.5-23.0 nm. Pattern B can be defined as smaller average particle sizes between about 18.0-20.5 nm.

As used herein, the term "small LDL particles" can include particles whose sizes range from between about 18.0 to about 21.2 nm. Alternatively, they can include particles in the very small (between about 18.0-19.8 nm) and intermediate small (between about 19.8-21.2 nm) diameter ranges. The term "large LDL particles" can include particles ranging in diameter between about 21.2-23.0 nm. Intermediate sized small particles may be parsed into one of the small and/or large designations or be measured separately as including particles in a size range that is typically near about 20.5 nm. It is noted that the LDL subclasses of particles can be divided in other size ranges. For example, small may be between about 18.0-20.5 nm, intermediate may be between about 20.5-21.2 nm, and large may be between about 21.2-23 nm. In addition, intermediate-density lipoprotein particles ("IDL" or "IDL-P"), which range in diameter from approximately 23.0-27.0 nm, can be included among the particles defined as LDL. The terms CAD and CHD are used interchangeably to correspond to a patient or subject's risk of developing or having coronary heart and/or artery disease.

The terms "population norm" and "standard" value associated with a lipoprotein measurement can be the values defined by the Framingham Offspring Study discussed below. However, the instant invention is not limited to these population values as the presently defined normal and at-risk population values for LDL particle concentrations or levels may change over time.

The flowcharts and block diagrams of certain of the figures herein illustrate the architecture, functionality, and operation of possible implementations of analysis models and evaluation systems and/or programs according to the present invention. In this regard, each block in the flow charts or block diagrams represents a module, segment, operation, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order, depending upon the functionality involved.

As is generally accepted, LDL-cholesterol levels provided by conventional lipid panels fail to sufficiently differentiate populations with and without CHD or CAD. As is known to those of skill in the art, the Framingham study proposed a relatively lengthy risk model that considers many factors such as age, gender, smoking habits, as well as cholesterol values. The research conducted in the Framingham Offspring Study also defined normative and at-risk population values from subjects in the study. See Wilson et al., *Impact of National Guidelines for Cholesterol Risk Factor Screening. The Framingham Offspring Study*, JAMA, 1989; 262: 41-44.

Unfortunately, many patients and clinicians still refer to total cholesterol and/or LDL-C and HDL-C to define a risk of developing CAD and/or to determine whether to begin or alter a therapeutic treatment. Thus, a simple, recognizable, easy-to-use more reliable risk factor may facilitate treatment for at-risk patients currently going undetected.

The present invention recognizes that lipoprotein particle physiology and/or properties can provide a better indicator of atherogenicity implicit to the lipoproteins that carry cholesterol. Since it is the number and size of lipoproteins that determine one's risk of heart disease—not one's cholesterol levels, drug therapy is typically targeted to reduce the number of LDL particles. Embodiments of the present invention are directed to providing an easy to recognize risk number that may facilitate treatment and follow-up that a patient and a clinician can use to more reliably assess risk relative to cholesterol risk factors commonly used. More aggressive treatments may be desired when certain LDL particle subclasses are present in borderline and/or increased amounts relative to the general population or a clinical baseline.

LDL is known to carry the so-called "bad" cholesterol. LDL particles come in different sizes. Conventionally, the smaller sizes have been thought to be the most dangerous type in that they were generally thought to be inherently more atherogenic than large particles. See, Sacks et al., *Clinical review 163: Cardiovascular endocrinology: Low density lipoprotein size and cardiovascular disease: a reappraisal*, J. Clin. Endocrinol Metab., 2003; 88; 4525-4532. Typical past studies examined only the distribution of LDL subclasses or LDL size phenotype (large or small) rather than particle concentrations of LDL subclasses. However, some studies have suggested that large LDL size may be associated with CHD. See, Campos et al., *Predominance of large LDL and reduced HDL2 cholesterol in normolipidemic men with coronary heart disease*, Arterioscler Thromb Vasc Biol., 1995; 15: 1043-1048; and Campos et al., *Low-density lipoprotein size, pravastatin treatment, and coronary events*, JAMA, 2001; 286, 1468-1474. Indeed, it is known that large LDL predominates in patients with familial hypercholesterolemia and those consuming high saturated fat diets. See, Patsch et al., *Characterization of lipoprotein in a kindred with familial hypercholesterolemia*, J. Lipid Res. 1982; 23:1 196-1205; and Dreon et al., *Change in dietary saturated fat intake is correlated with change in mass of large low-density-lipoprotein particles in men*, Am. J Clin Nutr 1998; 67: 828-836.

Despite the above, it is believed that, in the past, risk associated with small and large LDL particles was not compared on a per particle basis with control for the inverse correlation between small and large LDL particles. Also, the risk associated with small and large LDL particles was confounded due to their differing association with other lipoproteins and traditional cardiovascular risk factors. See e.g., Mora et al., *Both Large and Small LDL Particle Concentrations are Independently Associated with Carotid Atherosclerosis in the Multi-Ethnic Study of Atherosclerosis (MESA)*, Abstract presented at 2005 Scientific Sessions of the American Heart Association, Dallas, Tex., Circulation. 2005; 112: II-802. See also, Rosenson et al., *Relations of lipoprotein subclass levels and low density lipoprotein size to progression of coronary artery disease in the Pravastatin Limitation of Atherosclerosis in Coronary Arteries (PLAC-1) trial*, Am J. Cardiol., 2002; 90:89-94. Embodiments of the instant invention weight LDL particles to assess risk recognizing that both large and small LDL subclasses are associated with atherosclerosis with insignificant (or no) additional contribution of LDL-C once the inverse correlation between the two subclasses is taken into account.

Not wanting to be limited to any one theory, it is contemplated that, on a per particle basis, large LDL particles (large LDL-p) can be associated with a greater amount of carotid atherosclerosis than small LDL particles (small LDL-p) and that small and large LDL are significantly associated with atherosclerosis independent of other risk factors. Carotid atherosclerosis measured non-invasively by ultrasound is closely related to all major cardiovascular risk factors and generally accepted to be a strong predictor of clinical cardiovascular disease. See, e.g., O'Leary et al., *Intima-media thickness; a tool for atherosclerosis imaging and event prediction*, Am. J. Cardiol., 2002; 90: 18L-21L.

The amount of cholesterol per LDL particle varies widely from person to person. One reason is that large LDL particles have higher cholesterol content than small LDL particles. But even among people with exactly the same numbers of small and large LDL particles, LDL cholesterol levels vary because of differences in the relative amounts of cholesterol and triglycerides inside the particles. As a consequence, LDL cholesterol levels are an imperfect surrogate measure of a patient's LDL particle numbers and the CHD risk that these particles confer. See, e.g., Cromwell et al., *Low-density lipoprotein particle number and risk for cardiovascular disease*, Curr. Atheroscler. Rep., 2004; 6:381-387.

The present invention recognizes that large and small LDL particles do not confer exactly the same CHD risk. As a result, even though total numbers of LDL particles predict CHD better than LDL cholesterol, a further improvement in risk prediction may be realized by employing at least one weighting factor that adjusts the measurement of one or more different LDL particle subclasses to account for their different contributions to atherosclerosis.

Figure 2:
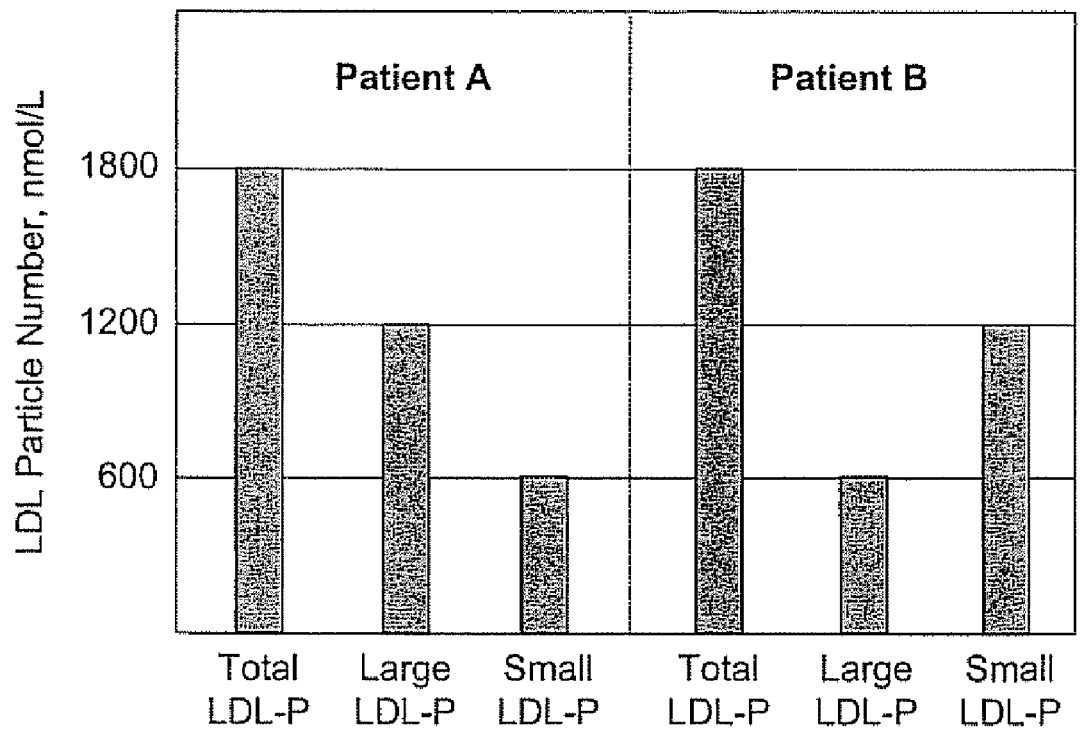
FIG. 2 is a schematic illustration of the dissimilar LDL subclass particle composition of two patients, both of whom have the same total number of LDL particles but dissimilar LDL-based risk of CHD as recognized according to embodiments of the present invention.

As an example, as shown in FIG. 2, consider two patients with the same number of LDL particles (LDL-P). Patient A has a greater number of large LDL particles and fewer small LDL particles than Patient B. If large LDL particles, on a, per particle basis, confer greater CHD risk, then the risk of Patient A would be greater than that of Patient B.

TABLE 1

| | LDL Particle Risk | |
|---|---|---|
| Type | Increment | Increase in IMT |
| Large LDL particles (nmol/L) | 220 | 40 microns |
| Small LDL particles (nmol/L) | 450 | 40 microns |

Table 1 is a table that compares prophetic carotid atherosclerosis data (as measured by carotid ultrasound and expressed as the increase in intima media thickness "IMT", associated with a given increment in concentration of large or small LDL) to illustrate that it can take more (shown as more than twice as much) small LDL particles to cause the same increase in atherosclerosis as caused by a lesser number of large LDL particles. As shown in this particular example, large LDL particles can be more (such as about 1.5-2.5 times more) atherogenic per particle than small LDL particles. This data is believed to be generally representative of findings in a study carried out using data from patients enrolled in the Multi-Ethnic Study of Atherosclerosis (MESA). See the Examples Section hereinbelow.

While not wishing to be bound by any one theory, it is possible that in vivo a relatively steady-state concentration of small LDL particles may travel from the blood stream past the endothelial cells and into the arterial intima due to their smaller size and/or cellular make-up, but that large LDL particles carry more atherogenic material, so a deposit of lesser numbers of large LDL particles can be problematic as well. Thus, a weighting factor applied to measures of large and/or small LDL particles in blood plasma and/or serum samples can provide a risk indicator of CAD risk.

In the past, an average LDL particle size of 20.5 nm might result from a sample having no large and no small LDL particles (all intermediate) as well as a sample having 50% large and 50% small (averaging to. an intermediate particle size). Hence, for a similar total LDL particle number, the CHD-risk for each of these samples may be different, but previously perhaps not clearly stated or easily recognized.

Certain embodiments of the present invention are directed at providing methods, systems, and computer program products that use LDL risk numbers and/or mathematical models that employ adjusted values of discrete measures of concentration of LDL subclasses of different (predetermined) particle size ranges that may simplify, improve and/or increase the predictive power of a risk analysis over a population. The models may be particularly useful in automated screening tests and/or risk assessment evaluations for CAD screening of in vitro biosamples.

In certain embodiments, a predetermined mathematical LDL subclass risk model can be configured to evaluate each measured amount of target (predetermined) LDL subclass and then determine the value of a predictor variable based on adjusted measurements of at least one different subclass (size range) of LDL particles. Embodiments of the invention can analyze samples to provide discrete concentration measurements for both small LDL particles and large LDL particles, recognizing that each size category has some degree of atherogenicity, and then calculate a predictor value considering each LDL subclass measurement.

In particular embodiments, an LDL particle risk predictor index or number ($Risk_{LDL}$) can be calculated by multiplying a weighting factor to at least one LDL subclass measurement, such as to either or both the amount of smaller LDL particles ($LDL_S$) and/or to the larger LDL particles ($LDL_L$) measured in the sample. If the weighting factor is only applied to the $LDL_S$ concentration, then it is presently contemplated that the weighting factor should be less than one, such as between about 0.25-0.75, and may be between about 0.5-0.7. If the weighting factor is applied only to the $LDL_L$ measurement, then the weighting factor may be between about 1.1 to about 2, and may be about 1.5+/−0.3. Exemplarily weights based on per particle measurements are provided below in Tables 2 and 3. Optimal weighting factors may be confirmed with data from further studies.

This LDL risk model may be expressed using the following mathematical equation:

$$X(LDL_S) + Y(LDL_L) = Risk_{LDL}.$$

where X or Y can be one, and/or where Y>X. In some embodiments, both weighting factors X and Y may be above 1.

In other embodiments, a third weighting factor "Z" can be used to add intermediate LDL particles and/or IDL particles to the model.

$$Z(IDL-P) + X(LDL_S) + Y(LDL_L) = Risk_{LDL}.$$

The third weighting factor Z may be greater than that of X and Y, and may have a value that is increased between about 4-6 above LDLs (relative to measurement of the small LDL particles). Hence, in certain embodiments: Z>Y>X.

Additional weights and LDL particle subclass subdivisions may be used. As an alternative to linear models primarily discussed herein, a multi-factorial (non-linear) model can be used to automatically calculate a risk number using an adjusted LDL subclass measurement obtained electronically based on a measurement of a biosample without requiring clinician input on non-automatically measured parameters (such as BMI, smoking habits and the like). The LDL subclass measurements can be combined and adjusted to automatically generate the LDL particle risk number, which can be electronically tracked over time.

In certain embodiments, X can be weighted above 1 and Y can be weighted above 1, to reflect the measured concentrations of the LDL particles' contribution to risk. In some embodiments, X can be weighted with a weighting factor that is below 1 and Y can be at about 1 or greater than 1. In other embodiments, X and Y can have weighting factors that are below 1, with Y being greater than X for certain or all measures of large LDL particle concentrations. In some embodiments, the subclass measurements can be adjusted so that the large LDL subclass measurement reflects between a 1.5-3 fold multiplier over the small LDL subclass measurement.

In particular embodiments, Y can be selected to increase the measured value of large LDL particles by at least about 25% relative to the small LDL particle measurement.

The weighting factors X, Y (and/or Z) in the model may be constants applied across substantially all samples. In other embodiments, the weighted values may be defined in situ and/or applied using a formula or a programmatically implemented or directed look-up table, based on a particular sample's contents. For example, X and Y may vary depending on age, gender, or other patient factor and/or based on the total LDL particles present, and/or the amount of each LDL subclass particle measured relative to the general population, and/or as a percentage of the LDL particles. For example, where large LDL subclass particles are present in an amount greater than the median value of the general population, a higher than normal weight can be assigned to Y. Where both small LDL particles and large LDL particles are present in amounts greater than the median of the general population, and/or the total LDL particle number is borderline or high, Y and/or both X and Y may be assigned a greater value compared to those situations where large and/or small LDL subclass particle numbers are less than the population median.

In certain embodiments, the model is configured to apply at least one different increased weighting factor, as increased concentrations of the small and/or large LDL particles are determined. Thus, for low levels of LDL, the LDL model used to determine the LDL risk number may not apply any weighting factors to the measured values of small and/or large LDL subclass particle concentrations to arrive at the risk number. However, as the total or individual concentrations of respective subclass particles approach a predetermined threshold level, a weighting factor(s) can then be applied or increased over lower LDL subclass concentrations.

In other embodiments, the mathematical model may employ different mathematical (non-linear) equations that increase the measured value of the small LDL particles in an in vitro sample to approximate the levels found within the arterial wall (such as in the endothelial space) in the body. As discussed above, other models may take into account age, gender, and the like, to adjust the concentration gradient for differences in endothelial cell physiology.

The predictive model can be used with any suitable LDL subclass measurement technique, including, but not limited to, gradient gel electrophoresis, density gradient ultracentrifugation, and NMR spectroscopy. However, in particular embodiments, the predictive model may be used with NMR spectroscopy measurements of LDL subclasses in in vitro blood plasma and/or serum samples.

In operation, to obtain the value of the predictor risk variable $R_{LDL}$, particle concentration measurements of at least large and small LDL particles in a sample of interest can be obtained (such as in nmol/L units or other suitable metric). If using NMR spectroscopy, then, similar to conventional techniques for NMR-derived particle concentration measurements, particle concentrations (nanomoles of particles per liter, nmol/L) for small and large LDL subclass particles can be calculated by measuring the signal amplitudes broadcast by these subclasses and applying conversion factors derived from the NMR measurements of isolated subclass standards of known particle concentration. The particle concentrations of the large and small LDL subclasses can then be adjusted (such as, for example, multiplied by their weighting factors (X, Y, etc.) and added together to provide the value of the $R_{LDL}$ (also typically in nmol/L)).

For example, compare two prophetic measurements of large and small LDL concentrations in two different patients, each having a total LDL particle number that is substantially the same, using the X (1.25) and Y (2.5) weighting factors to calculate an associated LDL risk number.

Patient (1)
L-LDLp 600 nmol/L
S-LDLp 800 nmol/L
$Risk_{LDL}=[(X)(800)+(Y)(600)]=2500$
Patient (2)
L-LDLp 400 nmol/L
S-LDLp 1000 nmol/L
$Risk_{LDL}=[X(1000)+Y(400)]=2250$ In other embodiments, the two prophetic measurements of large and small LDL concentrations in the two different patients can be adjusted using X=1 and Y=1.5 (making X=1 and adjusting Y so that the weighted large LDL measurement can generate the relative increase in risk) to calculate an associated LDL risk number.

Patient (1)
$Risk_{LDL}=[(X)(800)+(Y)(600)]=1700$
Patient (2)
$Risk_{LDL}=[X(1000)+Y(400)]=1600$ Thus, although each patient has a similar total LDLp number, patient (1) has a higher risk of CAD than patient (2) according to the LDL risk number.

For user ease of recognition, the risk number can be converted to a straight or scalar risk number, i.e., 1-10, or used as the risk number itself. For example, patients (1) and (2) can be assigned the risk number calculated above, or the number may be scaled in a particular way. For example, patient (1) may have a risk index of 8, while patient (2) may have a risk index of 7.

In contrast to previous analysis methods, two people having the same LDL particle number may now have a different adjusted (weighted) LDL risk number based on a weighted concentration of one or more of the constituents that make up the LDL particle number that may more appropriately represent the LDL-based risk in the person having increased amounts of larger LDL particles without disregarding risk from smaller LDL particles.

In any event, conventionally, the first step in treating increased numbers of lipoproteins is identification. Embodiments of the present invention provide screening tests and reports that analyze the unique properties of lipoproteins to give complete quantitative and qualitative lipoprotein information. The test report can be configured to contain significant and unique information about an individual's underlying risk for the metabolic syndrome including the LDL risk predictor variable $R_{LDL}$ (i.e., an adjusted LDL particle number) that can be used to assess the LDL particle-related risk in the lipoprotein risk analysis section as shown in FIG. 3. In addition, the $R_{LDL}$ parameter may replace the small LDL subclass and/or elevated LDL particle number shown in the risk assessment panel in FIG. 3.

As noted above, particular embodiments of the present invention are directed to NMR-derived measurements of lipoproteins similar to a NMR LipoProfile® NMR-derived cholesterol or lipoprotein panel, which includes a $R_{LDL}$ number as well as values for other lipoproteins of interest that may also be considered when evaluating a patient, including concentrations of subclasses of HDL and subclasses of VLDL.

Exemplary NMR Sample Analysis

As is known, an NMR lipoprotein subclass analysis can be carried out to measure lipoprotein subclass levels and average VLDL, LDL, and HDL particle diameters by NMR spectroscopy. The NMR method uses the characteristic signals broadcast by lipoprotein subclasses of different size as the basis of their quantification. See Otvos J D, Jeyarajah E J, Bennett D W, Krauss R M. *Development of a protein nuclear magnetic resonance spectroscopic method for determining plasma lipoprotein concentration and subspecies distributions from a single, rapid measurement*, Clin Chem 1992;38:1632-1638; and Otvos J D, *Measurement of lipoprotein subclass profiles by nuclear magnetic resonance spectroscopy*, Clin Lab 2002; 48-171-180. Each subclass signal emanates from the aggregate number of terminal methyl groups on the lipids contained within the particle, with the cholesterol esters and triglycerides in the particle core each contributing three methyl groups and the phospholipids and unesterified cholesterol in the surface shell each contributing two methyl groups. The total number of methyl groups contained within a subclass particle is, to a close approximation, dependent only on the particle's diameter and is substantially unaffected by differences in lipid composition arising from such sources as variability in the relative amounts of cholesterol ester and triglyceride in the particle core, varying degrees of unsaturation of the lipid fatty acyl chains, or varying phospholipid composition. For this reason, the methyl NMR signal emitted by each subclass serves as a direct measure of the particle concentration of that subclass.

In the past, NMR spectra of each plasma specimen (0.25 ml) were acquired in replicate (typically about 5 separate spectra are acquired) using an automated 400 MHz lipoprotein analyzer and the lipid methyl signal envelope decomposed computationally to give the amplitudes of the contributing signals of 16 lipoprotein subclasses (chylomicrons, 6 VLDL, 1 IDL, 3 LDL, 5 HDL). Conversion factors relating these signal amplitudes to subclass concentrations expressed in particle concentration units or lipid mass concentration units (cholesterol or triglyceride) were then applied. The conversion factors were derived from NMR and chemical analyses performed on a set of purified subclass standards of defined size, which were isolated from a diverse group of normo- and dyslipidemic individuals using a combination of ultracentrifugation and agarose gel filtration chromatography. Particle concentrations (in nmol/L (nmol of particles per liter)) were calculated for each subclass standard by measuring the total concentration of core lipid (cholesterol ester plus triglyceride) and dividing the volume occupied by these lipids by the core volume per particle calculated from knowledge of the particle's diameter. Rifai N, Warnick G R, Dominiczak M H, eds: *Handbook of LipoProtein Testing, 2nd Edition*, Washington, D.C., AACC Press; 2000, pp 609-623. Lipid mass concentrations of VLDL subclasses are given in mg/dL triglyceride units and those of the LDL and HDL subclasses in mg/dL cholesterol units. Summing the relevant subclass concentrations gives NMR-derived values for total VLDL triglycerides, LDL cholesterol, and HDL cholesterol.

Conventionally, the 16 measured subclasses have been grouped for analysis into the following 10 subclass categories (but different size ranges may also be used as noted above): large VLDL (60-200 nm), medium VLDL (35-60 nm), small VLDL (27-35 nm), IDL (23-27 nm), large LDL (21.3-23 nm), medium LDL (19.8-21.2 nm), small LDL (18.3-19.7 nm), large HDL (8.8-13 nm), medium HDL (8.2-8.8 nm), and small HDL (7.3-8.2 nm). IDL and LDL subclass diameters, which are uniformly ~5 nm smaller than those estimated by gradient gel electrophoresis, are consistent with both electron microscopy and LDL lipid compositional data. See Redgrave T G, Carlson L A, *Changes in plasma very low density and low density lipoprotein content, composition, and size after a fatty meal in normo- and hypertriglyceridemic man*. J Lipid Res. 1979;20;217-29; and Rumsey S C, Galeano N F, Arad Y, Deckelbaum R J. *Cryopreservation with sucrose maintains normal physical and biological properties of human plasma low density lipoproteins*, J Lipid Res 1992;33:1551-1561.

Weighted average VLDL, LDL, and HDL particle sizes (nm diameter) were computed as the sum of the diameter of each subclass multiplied by its relative mass percentage as estimated from the amplitude of its methyl NMR signal. LDL and HDL subclass distributions determined by gradient gel electrophoresis and NMR are highly correlated. Otvos J D, *Measurement of lipoprotein subclass profiles by nuclear magnetic resonance spectroscopy*, Clin Lab 2002; 48:171-180; and McNamara J R, Small D M, Li Z, Schaefer E J, *Differences in LDL subspecies involve alterations in lipid composition and conformational changes in apolipoprotein B*, J Lipid Res 1996; 37:1924-1935; and Grundy S M, Vega G L, Otvos J D, Rainwater D L, Cohen J C. *Hepatic lipase influences high density lipoprotein subclass distribution in normotriglyceridemic men: genetic and pharmacological evidence*, J Lipid Res 1999; 40:229-234.

Replicate analyses of plasma pools indicate that NMR subclass measurements are reproducible, with coefficients of variation <3% for NMR-derived values for total and VLDL triglycerides, LDL and HDL cholesterol, and LDL particle concentration, <4% for VLDL size, and <1% for LDL and HDL average size. Otvos J D, *Measurement of lipoprotein subclass profiles by nuclear magnetic resonance spectroscopy*, Clin Lab 2002; 48:171-180.

As noted above, the conventional analysis technique described has been modified to be able to reliably quantify large and small LDL particle concentrations as described in the aforementioned co-pending U.S. patent application Ser. No. 10/691,103. The evaluation can be further modified to implement a predictive model to provide a weighted LDL risk number according to embodiments of the present invention.

An alternative NMR measurement technique is described in *Diffusion ordered nuclear magnetic resonance spectroscopy: principles and applications*, Prog. In NMR Spec, 34 (1999) 203-256. See also, WO 2005/119285 A1, Process of Determination of Lipoproteins in Body Fluid, the contents of which are hereby incorporated by reference as if recited in full herein.

In addition, as noted above, other evaluation techniques (including non-NMR measurement techniques) may also be used according to alternative embodiments of the present invention.

Statistical Operations

In certain embodiments, the methods, systems, and/or computer products used to evaluate specimens employ statistical fitting models which evaluate signal data of an unknown sample according to a predetermined fitting model and standards to identify the presence of at least one selected chemical constituent and/or to measure the level or concentration thereof in the sample. More typically, the models, programs, and methods of the present invention are configured to evaluate signal data of a composite sample with highly or closely correlated individual constituent spectra (having at least a plurality with overlapping signal lines in the spectrum) to identify the presence of at least 10 different individual constituents and/or the level thereof. The term "highly" and "closely" are used interchangeably when used with "correlated" so that in the description that follows either "highly correlated" or "closely correlated" means that a plurality of constituents in a sample being analyzed generate respective spectra which can overlap in a composite signal that includes spectral contributions from those constituents.

As will be appreciated by one of skill in the art, the present invention may be embodied as an apparatus, a method, data or signal processing system, or computer program product. Accordingly, the present invention may take the form of an entirely software embodiment, or an embodiment combining software and hardware aspects. Furthermore, certain embodiments of the present invention may take the form of a computer program product on a computer-usable storage medium having computer-usable program code means embodied in the medium. Any suitable computer readable medium may be utilized including hard disks, CD-ROMs, optical storage devices, or magnetic storage devices.

The computer-usable or computer-readable medium may be, but is not limited to, an electronic, magnetic, optical, electromagnetic, infrared, or semiconductor system, apparatus, device, or propagation medium. More specific examples (a nonexhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted or otherwise processed in a suitable manner if necessary, and then stored in a computer memory.

Computer program code for carrying out operations of the present invention may be written in an object oriented programming language such as Java®, Smalltalk, Python, Labview, C++, or VisualBasic. However, the computer program code for carrying out operations of the present invention may also be written in conventional procedural programming languages, such as the "C" programming language or even assembly language. The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

The flowcharts and block diagrams of certain of the figures herein illustrate the architecture, functionality, and operation of possible implementations of analysis models and evaluation systems and/or programs according to the present invention. In this regard, each block in the flow charts or block diagrams represents a module, segment, operation, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order, depending upon the functionality involved.

Figure 4:
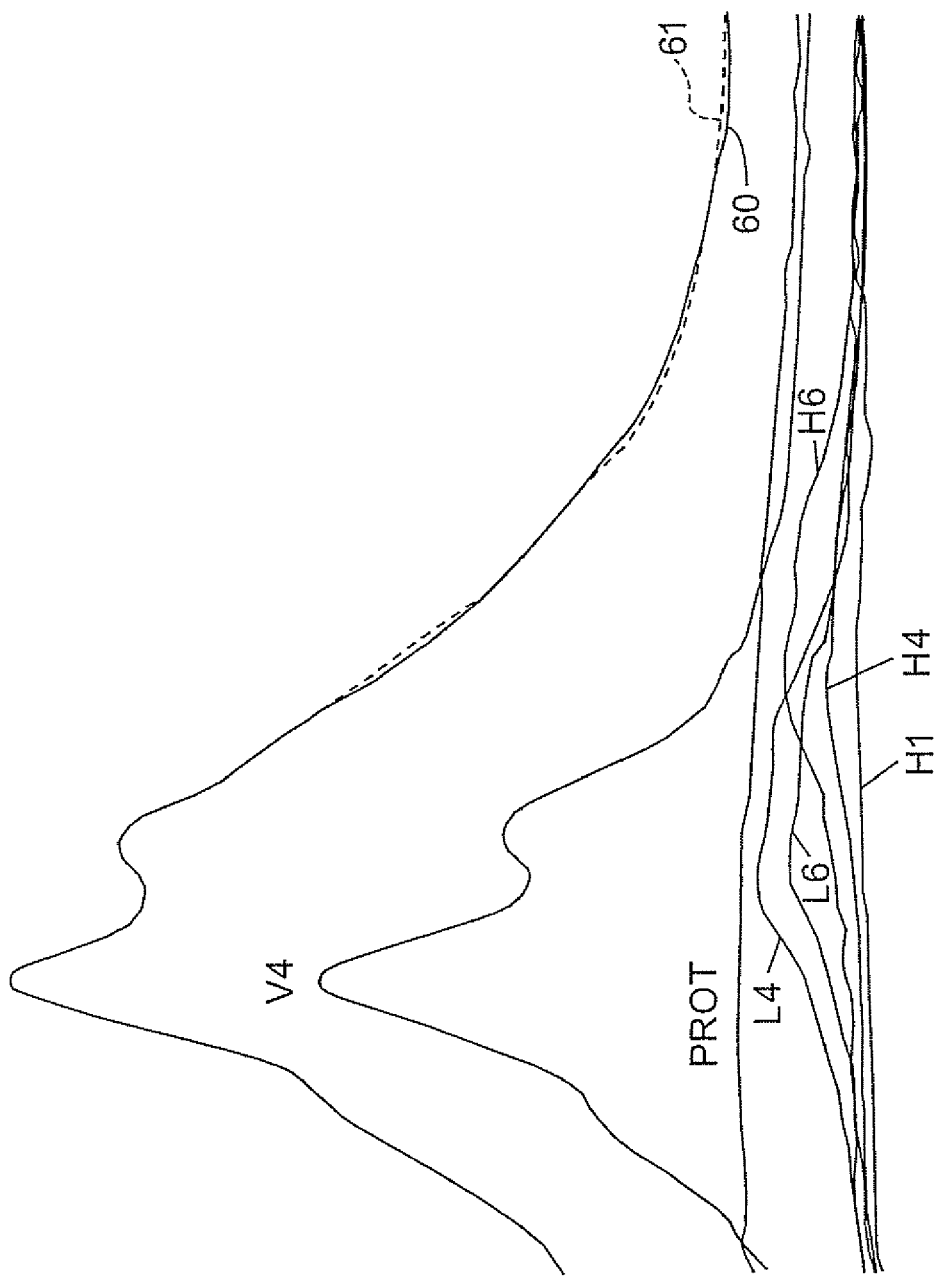
FIG. 4 is a graph illustrating NMR spectra for a composite plasma sample and the lipoprotein subclass and protein components thereof, with the peaks for methyl groups being illustrated.

The small person-to-person variations in the lineshapes of the lipoprotein classes are caused by the subclass heterogeneity known to exist within each of these lipoprotein classes. FIG. 1 shows the lineshapes and chemical shifts (positions) for a number of subclasses of lipoproteins. As shown in FIG. 1, the chemical shifts and lineshape differences between the different subclasses are much smaller than those between the major lipoprotein classes, but are completely reproducible. Thus, differences among the NMR signals from the plasma of individuals are caused by differences in the amplitudes of the lipid resonances from the subclasses present in the plasma, which in turn are proportional to their concentrations in the plasma. This is illustrated in FIG. 4, in which the NMR chemical shift spectra of a blood plasma sample is shown. The spectral peak produced by methyl ($CH_3$) protons 60 (shown as a solid line) is shown for the blood sample in FIG. 4. The spectral peak 61 (shown as a dotted line) in FIG. 4 is produced by the arithmetic sum of the NMR signals produced by the lipoprotein subclasses of the major classes VLDL, LDL, HDL, proteins and chylomicrons, as illustratively shown by certain of the subclasses in FIG. 1. It can be seen that the lineshape of the whole plasma spectrum is dependent on the relative amounts of the lipoprotein subclasses whose amplitudes chance (sometimes dramatically) with their relative concentrations in the plasma sample.

Since the observed $CH_3$ lineshapes of whole plasma samples are closely simulated by the appropriately weighted sum of lipid signals of its constituent lipoprotein classes, it is possible to extract the concentrations of these constituents present in any sample. This is accomplished by calculating the weighting factors which give the best fit between observed blood plasma NMR spectra and the calculated blood plasma spectra. Generally speaking, the process of NMR lipoprotein analysis can be carried out by the following steps: (1) acquisition of an NMR "reference" spectrum for each of the "pure" individual or related groupings of constituent lipoprotein classes and/or subclasses of plasma of interest, (2) acquisition of a whole plasma NMR spectrum for a sample using measurement conditions substantially identical to those used to obtain the reference spectra, and (3) computer deconvolution of the plasma NMR spectrum in terms of the constituent classes and/or subclasses (or related groupings thereof) to give the concentration of each lipoprotein constituent expressed as a multiple of the concentration of the corresponding lipoprotein reference.

Although the procedure can be carried out on lipoprotein classes, carrying out the process for subclasses of lipoproteins can decrease the error between the calculated lineshape and the NMR lineshape, thus increasing the accuracy of the measurement while allowing for simultaneous determination of the subclass profile of each class. Because the differences in subclass lineshapes and chemical shifts are small, it is typically important to correctly align the reference spectrum of each subclass with the plasma spectrum. The alignment of these spectra is accomplished by the alignment of control peaks in the spectra, which are known to respond in the same manner to environmental variables, such as temperature and sample composition, as do the lipoprotein spectra. One such suitable alignment peak is the peak produced by CaEDTA, although other EDTA peaks or suitable peak may be utilized. By alignment of the spectra, the small variations in the subclasses' lineshapes and chemical shifts may be exploited to produce higher accuracy and subclass profiles.

Further description of these methods can be found in U.S. Pat. Nos. 4,933,844 and 5,343,389 to Otvos.

Lineshape

The mathematics used in the lineshape fitting process (i.e., least squares fit of an unknown function in terms of a weighted sum of known functions) is well known and is described in many textbooks of numerical analysis, such as F. B. Hildebrand, *Introduction to Numerical Analysis*, 2nd edition, pp. 314-326, 539-567, McGraw-Hill, 1975.

In particular embodiments, reference samples of each constituent lipoprotein and protein component to be analyzed are prepared (typically they are refrigerated during storage and allowed to warm prior to analysis) and placed within the spectrometer 10. An NMR measurement is then taken on each reference sample to define a standard for the respective constituent. The data for the reference samples (for a plurality of different constituents) is processed and stored in the computer 11. Techniques for acquiring and storing NMR spectroscopic data are well-known to those skilled in this art and need not be described in further detail. The reference samples or standards may be established a priori and used to measure a plurality of different patient specimens or samples over time.

To carry out the analysis, the data points of the real part of the sample plasma spectrum that comprise the spectral region to be fit (normally 0.73-0.85 ppm for lipoprotein evaluations) are entered into an array. This plasma array consists of m discrete data points denoted $P_i^o$, i=1,2, ... m. The data points of the real part of the lipoprotein subspecies reference spectra for the same spectral region are entered into separate arrays. The data points of these arrays are denoted $V_{ji}$, where i=1, 2, ... m data points and j=1,2, ... n constituents). It is noted that in the Equations and text describing same that follows, some symbols may be bolded and/or italicized at certain locations but not at other locations, however this is not meant to alter the correlation or change the meaning of the symbol herein.

The method for fitting the measured sample plasma spectrum, $P_i^o$, with a linear combination of n constituent spectra is based on the premise that there are a set of coefficients (weighting factors), $c_j$, corresponding to the contributions of component j (lipoprotein subclass components and protein component), and a coefficient, $c_p^I$, corresponding to the imaginary portion of the sample plasma spectrum, such that for each data point, $P_i^o \approx P_i^c$, where $$P_i^c = \left(\sum_{j=1}^{n} c_j V_{ji}\right) + c_p^I V_i^I \text{ (calculated plasma spectrum)} \quad (1)$$

In the past, the best fit was achieved when the root mean square error, $$\sqrt{\frac{1}{m-n}(\sum \epsilon_i^2)} \quad (2)$$

was minimized, where $\epsilon_i = P_i^o - P_i^c$. This was accomplished by finding those coefficients which minimize $\Sigma \epsilon_i^2$, that is, when $$\frac{\partial \sum \epsilon_i^2}{\partial c_j} = 0, \quad (3)$$

j=1,2, ... n+1 (n−1 subspecies components plus protein and plasma spectrum phase contributions). Differentiation results in n+1 simultaneous linear equations:

$$\sum_{i=1}^{m} P_i^o V_{ki} = \sum_{j=1}^{n+1} c_j \left( \sum_{j=1}^{M} V_{ki} V_{ji} \right), k = 1, 2, \ldots n+1 \quad (4)$$

If $$a_{kj} = \sum_{j=1}^{m} V_{ki} V_{ji} \text{ and } s_k = \sum_{i=1}^{m} P_i^o V_{ki} \quad (5)$$

then there are n+1 simultaneous linear equations of the form:

$$\sum_{j=1}^{m} c_j a_{kj} = s_k, k = 1, 2, \ldots n+1 \quad (6)$$

Forming the n+1×n+1 matrix, [A]=[$a_{kj}$], j=1,2 ... n+1; k=1,2 ... n+1, gives [A]C=S, where C and S are the column vectors, $$\begin{bmatrix} c_1 \\ c_2 \\ \vdots \\ c_n \\ c_{n+1} \end{bmatrix} \text{ and } \begin{bmatrix} s_1 \\ s_2 \\ \vdots \\ s_n \\ s_{n+1} \end{bmatrix} \quad (7)$$

The coefficients providing the best fit were calculated by decomposition of the matrix [A] into a new set of m×m matrices known collectively as the "singular value decomposition" of [A]:

$$[A]=[U][W][V]^T \quad (8)$$

where [U] is a matrix of orthogonal column vectors (scalar products =0), [V]$^T$ is the transpose of an orthogonal matrix [V], and [W] is a diagonal matrix with positive or zero elements, called "singular values:"

$$[W] = \begin{bmatrix} w_1 & 0 & \cdots & 0 \\ 0 & w_2 & \cdots & 0 \\ \vdots & \vdots & \ddots & \vdots \\ 0 & 0 & \cdots & w_m \end{bmatrix} \quad (9)$$

From this, $$[A]^{-1}=[V][W]^{-1}[U]^T \quad (10)$$

where $$[W]^{-1} = \begin{bmatrix} 1/w_1 & 0 & \cdots & 0 \\ 0 & 1/w_2 & \cdots & 0 \\ \vdots & \vdots & \ddots & \vdots \\ 0 & 0 & \cdots & 1/w_m \end{bmatrix} \quad (11)$$

which allows C to be solved for:

$$C=[V][W]^{-1}[U]^T S \quad (12)$$

where C was the best possible solution vector, provided that values of $w_j$ below a certain threshold value (selected by the user) are ignored ($1/w_j$ set to zero). These singular values can give rise to "ill-conditioned" linear combinations of near degenerate solutions, being most corrupted by roundoff errors. The actual solution of C was obtained by "back-substitution" in which $w_m$ is determined, allowing for the solution of $w_{m-1}$, etc.

The root mean square deviation (RMSD) is computed as $$\sigma_{RMS} = \sqrt{\frac{1}{m-n-1} \sum_{i=1}^{m} (P_i^o - P_i^c)^2} \quad (13)$$

The correlation coefficient was computed as $$r^P = \frac{\sum_{i=1}^{m} (P_i^o - \langle P_i^o \rangle)(P_i^c - \langle P_i^c \rangle)}{\sqrt{\left( \sum_{i=1}^{m} (P_i^o - \langle P_i^o \rangle)^2 \sum_{i=1}^{m} (P_i^c - \langle P_i^c \rangle)^2 \right)}} \quad (14)$$

In the past, the component coefficients resulting from this lineshape analysis provided the concentrations of the lipoprotein and protein constituents in each plasma sample. Each concentration can be expressed relative to the concentration of the lipoprotein whose spectrum is used as the reference. In operation, the final concentrations may be normalized to the integrated area of the resonance from a tri-methylacetate external standard sample run on the same day to correct for variations in the detection sensitivity of the NMR spectrometer.

As described above, the least squares method used in the past for NMR-derived measurement of lipoprotein subclasses required that the derived concentrations be a positive value. Generally described, in the past, when a negative coefficient for a selected constituent associated with one of the standards was encountered it was constrained to zero, and the calculation was performed again, subject to that constraint. The latter constraint can be desirable when fitting plasma samples that may not contain one or more of the components included in the fit model or because experimental errors in the data (noise) can cause the calculation to give negative values for concentrations for these components.

Figure 5:
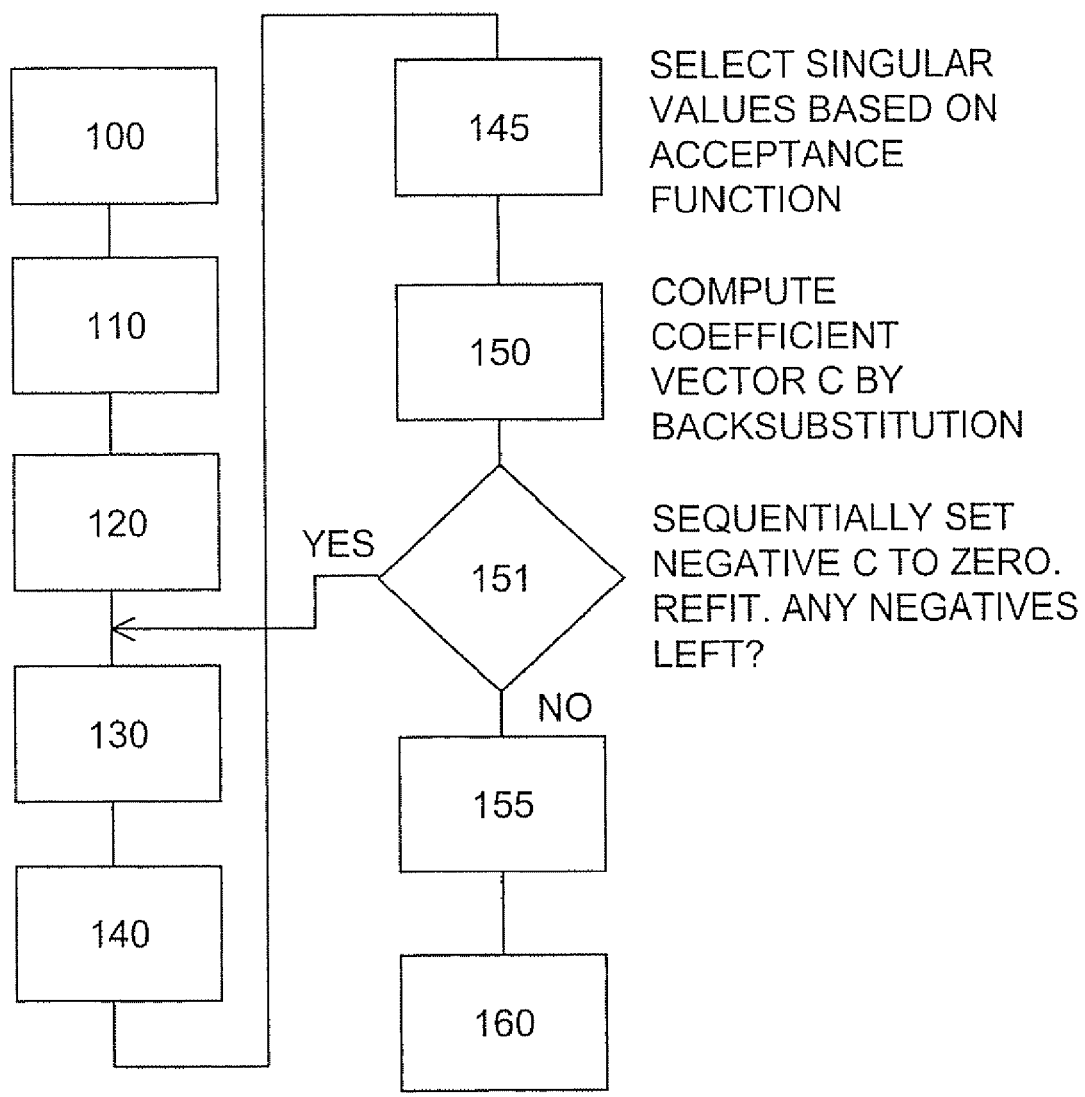
FIG. 5 is a block diagram of operations that can be used to evaluate signal data according to embodiments of the present invention.

FIG. 5 illustrates a flow chart of operations with reference to certain of the above-stated equations in blocks 100-160. In operation, spectra of subspecies components are read into Array V (block 100). The real part of the sample plasma spectrum is read into Array P$^0$ (block 110). The imaginary part of the sample plasma spectrum is read into the Array V (block 120). Marix [A] and S vector are calculated (block 130) using Equation 5. Matrix [A] is decomposed into a singular value decomposition (block 140) such as by using Equation 8. The singular values are selected based on a predetermined acceptance function (block 145). The coefficient vector C is calculated using back substitution (block 150). The negative values in C are sequentially set to zero and the curve is refit, until there are no negatives left. The yes or no inquiry at (block 151) asks whether there are negatives left and, if so, directs the program to return to the operation in (block 130) and, if not, directs the operations to advance to (block 155). C is multiplied by normalization constants to obtain concentrations (block 155). The root mean square deviation and correlation coefficient are calculated (block 160) such as by using Equations 13 and 14.

Embodiments of the present invention modify and improve on the conventional protocol by employing operations that can reduce measurement variability in individual constituents and/or by reducing the number of constituents of interest that are reported as having a "0" value. The variability can be assessed by repeatedly analyzing a given sample and measuring the individual constituents. The individual constituents measured by the present invention will typically be clustered more tightly together relative to the individual constituents measured by the conventional protocol. The methods and systems can reduce the variability by at least about 50% relative to the prior method for the same sample. Further, when analyzing the same sample in repeated interrogations, the measured values of at least a majority of the constituents of interest, if not all of the constituents of interest, can be reproducible, typically within about +/−2.34% (median CV).

Figure 6:
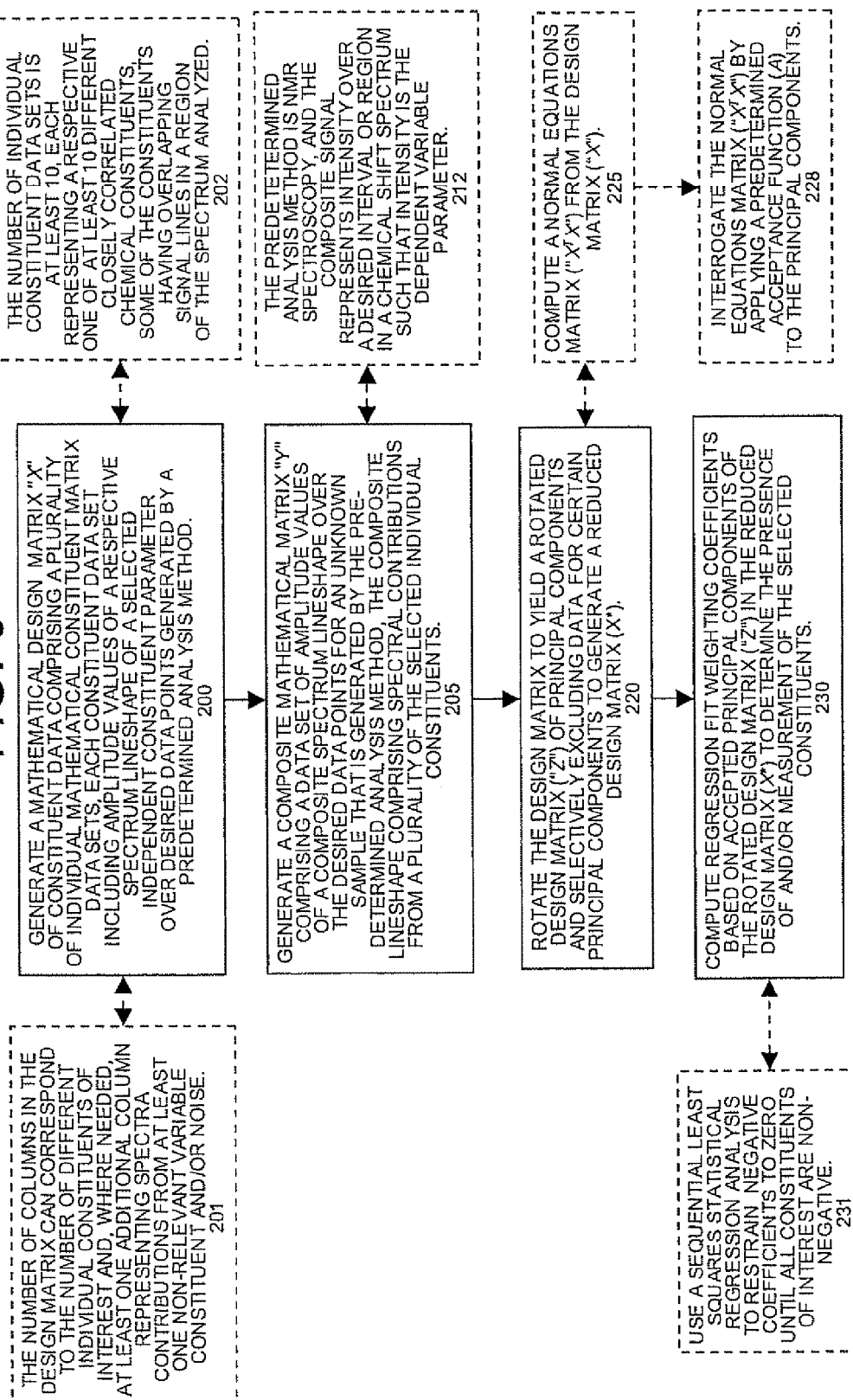
FIG. 6 is a block diagram of operations that can be used to evaluate signal data according to embodiments of the present invention.

Referring now to FIG. 6, operations of certain embodiments of the invention are illustrated. It is noted that the term "matrix," as used herein, can, in certain embodiments, be a vector, as a vector is a special form of a matrix (i.e., a vector is a matrix with n rows and 1 column, or 1 row and k columns). As shown in FIG. 6, the operations can include generating a mathematical design matrix of constituent data comprising a plurality of mathematical constituent matrix data sets, each constituent data set including amplitude values of a respective spectrum lineshape of a selected independent constituent parameter over desired data points generated by a predetermined analysis method (of a known reference sample) (block 200). The selected constituent parameter (the independent parameter) can be wavelength, voltage, current, speed, force, torque, pressure, movement, energy, chemical shift (ppm), temperature, frequency. Exemplary dependent parameters of interest may include, but are not limited to, intensity, opacity, transmittance, reflectance, fluorescence, vibration, or other desired parameter. The constituent data of the design matrix ("X") can be reference or standard data established a priori from separate individual analysis of discrete constituents of interest and/or stored in an accessible database to be used as a standard and applied in analysis of all or selected ones of unknown samples.

A composite mathematical matrix can be generated comprising a data set of amplitude values of a composite spectrum lineshape over the desired data points for an unknown sample that is generated by a predetermined analysis method. The composite lineshape comprises spectral contributions from a plurality of the selected individual constituents (block 205). The design matrix can be rotated to yield a rotated design matrix of principal components (which may, in certain embodiments, be mathematically represented by matrix "Z" as will be discussed further below) and processed to selectively exclude data for certain principal components to generate a reduced design matrix (which may, in certain embodiments, be represented mathematically by matrix "X*" as will be discussed further below) (block 220). The term "principal components" means individual identifiable constituents (and may include both relevant and non-relevant constituents) in the rotated space. In operation, in certain embodiments, the operations can include mathematically rotating the design matrix, interrogating the rotated design matrix (using an acceptance function) to find those rotated principal components with contributions that benefit the deconvolution, and rotating back those accepted principal components to form the reduced design matrix.

In certain embodiments, a normal equations matrix (which, in certain embodiments, may be mathematically represented by matrix "$X^TX$") can be computed from the design matrix (block 225). The normal equations matrix can be interrogated by applying a predetermined acceptance function ("$A(\lambda)$") to the principal components to generate the reduced design matrix. The acceptance function can be a forced logic function of "0" and "1" (representative of rejected (excluded) values and accepted (included) values, respectively) or may be a relative or absolute function that discards the principal components having values low with respect to other components or relative to a predefined threshold (i.e., the values having the least significance) and retaining the more significant values in the reduced design matrix. The reduced matrix may be generated by rotating the design matrix and eliminating the column or columns in the rotated design matrix with the most "0"s as determined by the acceptance function.

Regression fit weighting coefficients can be computed based on accepted principal components of the rotated design matrix in the reduced design matrix to determine the presence of and/or measurement of the selected or target constituents in the unknown sample undergoing analysis (block 230). In particular embodiments, the weighting coefficients may be determined according to Equation (21) as will be discussed further below. A sequential least squares regression analysis can then be employed to restrict or restrain negative coefficients to zero until all (or substantially all) constituents of interest are non-negative (block 231). In certain embodiments, before the sequential regression analysis evaluation is performed, the reduced design matrix is combined with the composite matrix to define a first set of weighting factors.

Described differently, the signal from the unknown test sample can be projected onto the space spanned by selected principal components and the projection coefficients can be transformed back into the original space to provide a reduced design matrix for arriving at weighting coefficients. As such, the design matrix can be mapped into the rotated design matrix and the components selected to yield the reduced design matrix.

The reduced design matrix can be generated based on predetermined criteria using a shrinkage estimator. In certain embodiments, the shrinkage estimator can be based on the spectral decomposition of a matrix defined by the multiplication of the constituent matrix with the transposed constituent matrix. In certain embodiments, the shrinkage estimator can be found by projecting the constituent matrix onto the space spanned by the accepted basis set determined from the rotation of the design matrix, and shrinking the projection of the constituent matrix on the orthogonal subspace to zero. A particularly suitable shrinkage estimator is described in Equation (21), It is noted that other shrinkage estimators may also be employed. Generally stated, a shrinkage estimator of a parameter b is any estimator B(X) of the data X such that $\|E\{B(X)\}\| \leq \|b\|$. A simple example would be to take an unbiased estimator of b, say U(X), and multiply by a constant smaller than 1: B(X)=pU(X) where 0<p<1. Because U(X) is unbiased, by definition of unbiased, E{U(X)}=b. Then the norm of the expectation could be expressed as ‖E{B(X)}‖=‖E{p U(X)}‖=p ‖E{U(X)}‖=p ‖b‖<‖b‖ since p<1. In the shrinkage estimator of Equation (21), shrinkage is carried out selectively, in the direction of zero for some components, and not for others.

The number of individual constituent data sets can be at least ten (10), each representing a respective one of at least ten (10) different closely correlated chemical constituents, some of the constituents having overlapping signal lines in a region of the spectrum analyzed (block 202). The number of columns in the design constituent matrix can correspond to the number of different individual constituents of interest, and, where needed, at least one additional column, which may be a matrix of variables, representing spectra contributions from at least one non-relevant variable constituent and/or noise (block 201). In operation, this additional column may not be used (i.e., "0"). The at least one non-relevant variable can be a constituent known to be in the sample but not a target interest and/or background or environmental noise, and the like.

In certain embodiments, the predetermined analysis method is NMR spectroscopy, and the composite signal represents intensity over a desired interval or region in a chemical shift spectrum (typically represented in ppm) such that intensity is the dependent variable parameter (block 212).

Figure 7:
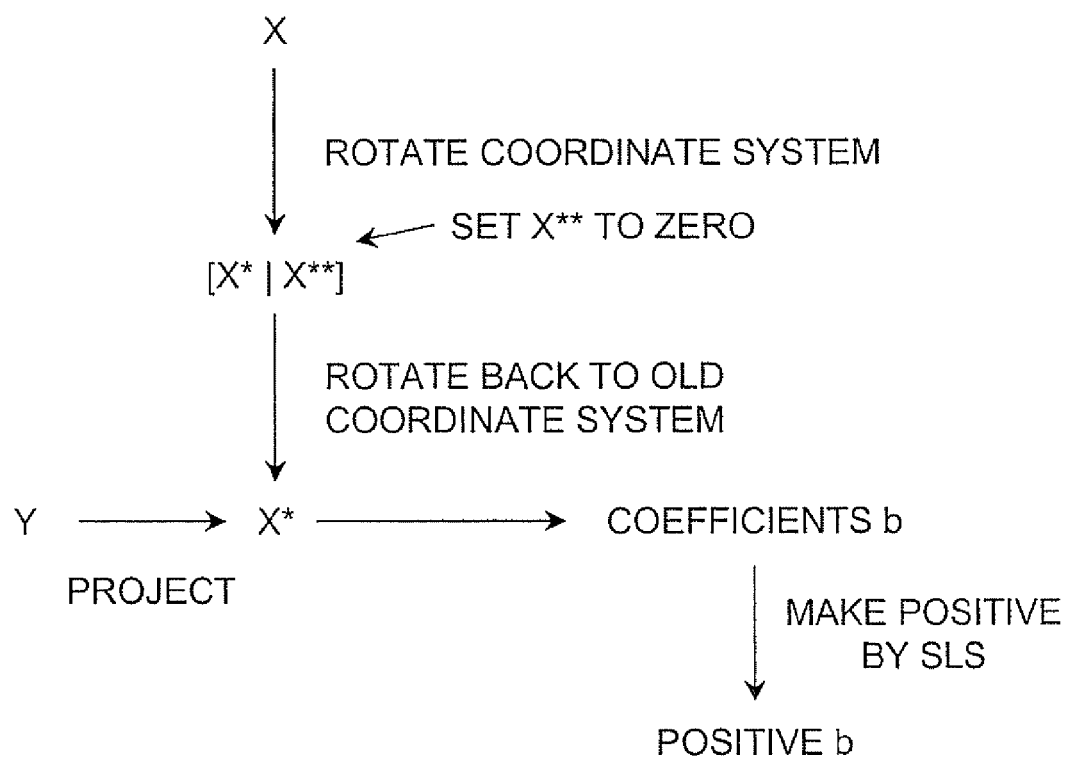
FIG. 7 is a schematic diagram of an interrogation protocol used to evaluate signal data for composite spectra having contributions from overlapping constituents according to embodiments of the present invention.

FIG. 7 is a schematic illustration of certain embodiments of the deconvolution operations used to evaluate closely correlated signal data. As shown, a design matrix "X" of constituent data comprising a plurality of individual mathematical data sets, each constituent data set including amplitude values of a respective spectrum lineshape of a selected constituent parameter over the variable space, spectrum length, or data points of interest, is obtained. The coordinate system of the design matrix is rotated to generate a rotated design matrix "Z" and, ultimately, a reduced design matrix "X*" (and a related transposed matrix "X**"). The line extending between X* and X** represents a classifier or acceptance function that determines what principal component data in X will be excluded from X*. The matrix is then rotated back to the original coordinate system, thereby generating a reduced design matrix "X*" with data from X modified by the analysis performed at the rotation of the coordinate system. The matrix of the composite spectrum lineshape data "Y" is projected onto X* and the weighting coefficients "b" calculated. A sequential least squares ("SLS") regression analysis is performed on the defined weighting coefficients to ensure that positive weighting coefficients are established. The operations may be iteratively repeated.

Figure 8:
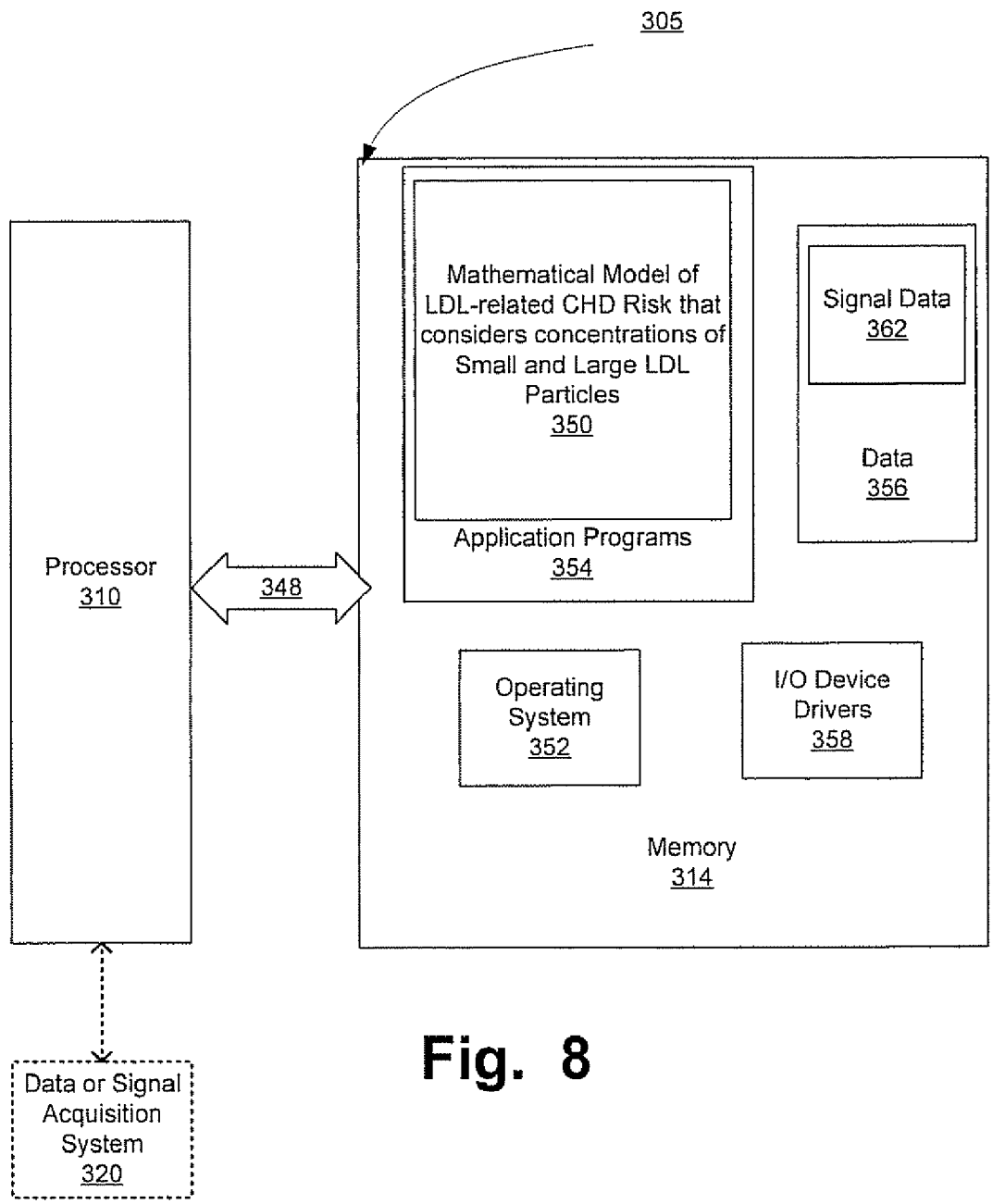
FIG. 8 is a schematic diagram of a data processing system according to embodiments of the present invention.

FIG. 8 is a block diagram of exemplary embodiments of data processing systems that illustrates systems, methods, and computer program products in accordance with embodiments of the present invention. The processor 310 communicates with the memory 314 via an address/data bus 348. The processor 310 can be any commercially available or custom microprocessor. The memory 314 is representative of the overall hierarchy of memory devices containing the software and data used to implement the functionality of the data processing system 305. The memory 314 can include, but is not limited to, the following types of devices: cache, ROM, PROM, EPROM, EEPROM, flash memory, SRAM, and DRAM.

As shown in FIG. 8, the memory 314 may include several categories of software and data used in the data processing system 305: the operating system 352; the application programs 354; the input/output (I/O) device drivers 358; a Module of a Mathematical Model of LDL-related CHD Risk that considers internal concentrations of small and large LDL particles 350; and the data 356. The LDL Predictive Risk Module 350 can include a mathematical model that employs a predetermined increased weighting factor for at least one LDL particle subclass to provide a weighted risk LDL particle number that adjusts the measured values in the blood or plasma sample.

The data 356 may include signal (constituent and/or composite spectrum lineshape) data 362 which may be obtained from a data or signal acquisition system 320. As will be appreciated by those of skill in the art, the operating system 352 may be any operating system suitable for use with a data processing system, such as OS/2, AIX or OS/390 from International Business Machines Corporation, Armonk, N.Y., WindowsCE, WindowsNT, Windows95, Windows98, Windows2000 or WindowsXP from Microsoft Corporation, Redmond, Wash., PalmOS from Palm, Inc., MacOS from Apple Computer, UNIX, FreeBSD, or Linux, proprietary operating systems or dedicated operating systems, for example, for embedded data processing systems.

The I/O device drivers 358 typically include software routines accessed through the operating system 352 by the application programs 354 to communicate with devices such as I/O data port(s), data storage 356 and certain memory 314 components and/or the image acquisition system 320. The application programs 354 are illustrative of the programs that implement the various features of the data processing system 305 and can include at least one application, which supports operations according to embodiments of the present invention. Finally, the data 356 represents the static and dynamic data used by the application programs 354, the operating system 352, the I/O device drivers 358, and other software programs that may reside in the memory 314.

While the present invention is illustrated, for example, with reference to the Module 350 being an application program in FIG. 8, as will be appreciated by those of skill in the art, other configurations may also be utilized while still benefiting from the teachings of the present invention. For example, the LDL risk Model Module 350 may also be incorporated into the operating system 352, the I/O device drivers 358 or other such logical division of the data processing system 305. Thus, the present invention should not be construed as limited to the configuration of FIG. 8, which is intended to encompass any configuration capable of carrying out the operations described herein.

In certain embodiments, the Module 350 includes computer program code for providing a single risk predictor number for LDL particles in a subject that can indicate whether therapy intervention is desired and/or track efficacy of a therapy using the risk predictor number as a sensitive reflection of what is occurring at the arterial wall.

For NMR derived lipoprotein measurements, the computer program code can include a sequential least squares regression analysis based on a statistical model comprising: (a) a mathematical composite matrix representing spectrum measurements of the amplitude of a composite signal of an unknown sample across "n" points in the spectrum; and (b) a design matrix including respective mathematical matrices for the amplitude of each of a plurality of individual selected constituents across "n" points in the spectrum. The shrinkage estimator and acceptance function can be used to generate optimum weighting factors "$b_{opt}$" for each constituent of interest based on the difference between the composite signal amplitude and the constituent amplitudes defined by interrogation of the values in the constituent and composite vectors.

The analysis can be iteratively repeated in a sequential least squares regression model until target or selected constituents have been assigned non-negative weighting factors such that a sequential least squares statistical evaluation produces a satisfactory non-negative solution set for the target constituents.

The I/O data port can be used to transfer information between the data processing system 305 and the image scanner or acquisition system 320 or another computer system or a network (e.g., the Internet) or to other devices controlled by the processor. These components may be conventional components such as those used in many conventional data processing systems, which may be configured in accordance with the present invention to operate as described herein.

While the present invention is illustrated, for example, with reference to particular divisions of programs, functions and memories, the present invention should not be construed as limited to such logical divisions. Thus, the present invention should not be construed as limited to the configuration of FIG. 8 but is intended to encompass any configuration capable of carrying out the operations described herein.

More particularly described, in particular embodiments, a target sample to be analyzed may have a number of different selected parts or constituents or individual or groupings of selected constituents. The number of constituent parts may be noted as k. Thus, a sample undergoing analysis can include constituent parts, $P_1, \ldots, P_k$. As noted above, the number k may be at least 10, and can be between 35-40 or even larger. The sample can be analyzed on a desired suitable analytical instrument, with the amplitude of the independent variable (e.g., intensity, wavelength, retention time, current, etc., as described above) varied. The amplitude or value of the independent constituent(s) varies corresponding to the detector response of the analytical instrument and the variation can be recorded in the form of a spectrum. The spectrum or lineshape consists of amplitude measurements (that may be intensity measurements in certain embodiments) at n points. These amplitude measurements of the sample being analyzed are stored in a composite matrix, Y.

Also, each constituent part, $P_j$, j=1 to k, is separately analyzed to define a standard or reference over the same independent variable space, region, or data points as the sample undergoing analysis. Each set of the respective reference constituent spectral amplitudes (such as intensities) are stored in a matrix $X_j$, where, j=1, ..., k, also of length n. Thus, a design constituent matrix X can be represented by:

$$X = [X_1, X_2, \ldots, X_k, Z] \quad (15)$$

where Z is a matrix of amplitude data regarding at least one additional variable that can be deconvolved from the spectral signal. For example, Z may contain data representing spectral intensities of other known or unknown constituents, the imaginary part of the spectrum of the analyte sample, (where Y contains the real part of the spectrum), noise, etc . . . However, it is noted that Z can be a matrix, a vector, or, in certain embodiments, even null (a degenerate form of matrix with 0 columns).

In certain embodiments, Z is a matrix of size n×w, where w≧0. In certain particular embodiments, w=1. The estimated contributions of the individual components to the sample or analyte composite spectrum can be found by determining a normalized or optimal coefficient weightings $b_{opt}$ given by equation 16. The normalized weighting coefficient minimizes the values inside the brackets of the arg $\min_b$ function.

$$b_{opt} = \arg\min_b \{\|Y - Xb\| : b \geq 0\}. \quad (16)$$

These normalized weightings can be found by solving equation (16) using a shrinkage estimator to the regression problem, followed by the application of non-negative least squares to ensure that the non-negativity constraint is satisfied. The cycle is repeated until the least squares solution provides only non-negative weighting factors. The shrinkage estimator can be based on the spectral decomposition of the matrix $M = X^T X$ where $X^T$ represents a transposition of the constituent matrix X. Further, the spectral decomposition matrix M may be expressed by the following:

$$M = Q\Lambda Q^T \quad (17)$$

where Q(k+w)×(k+w) is orthogonal, and Λ (k+w)×(k+w) is a diagonal matrix comprising eioenvalues. The eigenvalue matrix Λ is sorted with the largest eigenvalue in the (1,1) element or position, the next largest value in the (2,2) element or position, and continuing left to right and top to bottom, etc . . . , until the smallest element is placed in the (n, n) element or position. An adjustable tolerance parameter "τ" can be defined such that τ≧0. Also an acceptance or classifier function "A" can be defined such that A(λ): Λ→{0, 1} which indicates which component is accepted into a fitting model.

A reduced eigenvalue matrix "$\Lambda_{red}$" can be defined as:

$$\Lambda = \Lambda_{red} = \Lambda \, \mathrm{diag}(A(\Lambda_{j,j})) \quad (18)$$

The X* matrix ("reduced design matrix") described above may be identified as:

$$X^* = Q \Lambda_{red}^{1/2} \quad (19)$$

One acceptance function that has been used is:

$$A(\lambda) = \begin{cases} 1 & \text{if } \lambda > \tau\Lambda_{1,1} \\ 0 & \text{otherwise} \end{cases} \quad (20)$$

where τ has been chosen to minimize Var b while maintaining E{b}. Examples of values for τ are in the range between $10^{-6}$ and $4 \times 10^{-6}$ for cases where k is about 37, i.e., where there are about 37 constituents or parts "$P_1$-$P_{37}$". Other values may be appropriate for lesser or greater numbers of constituents. Then b can be calculated as:

$$b = Q\Lambda_{red}^{-1} Q^T X^T Y \quad (21)$$

Figure 9:
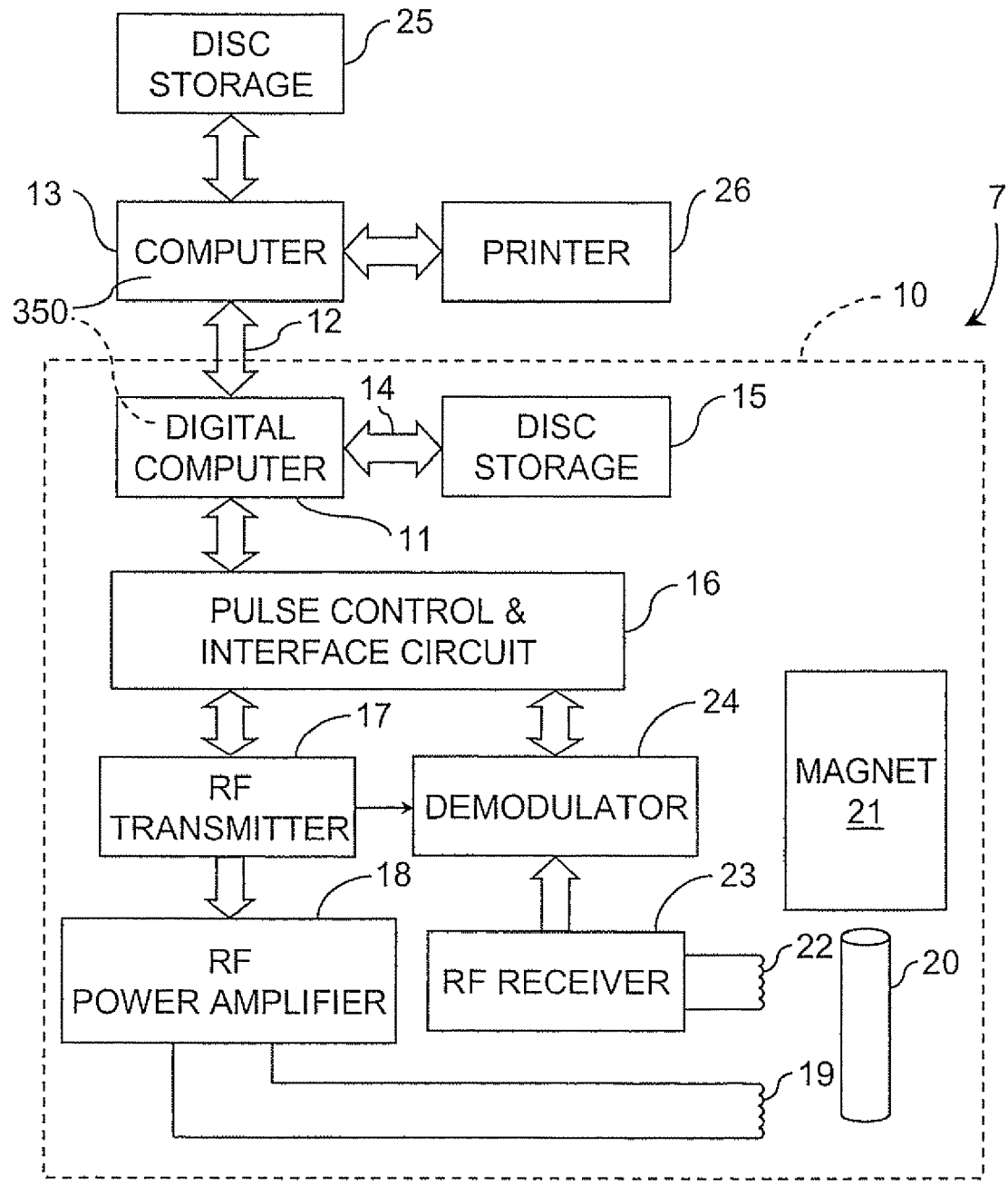
FIG. 9 is a schematic illustration of a NMR spectroscopy apparatus according to embodiments of the present invention.

Configuration of Exemplary System for Acquiring and Calculating Adjusted LDL Particle Subclass Concentration Measurements and/or LDL Particle Risk Number Referring now to FIG. 9, a system 7 for acquiring and calculating the lineshape of a selected sample is illustrated. The system 7 includes an NMR spectrometer 10 for taking NMR measurements of a sample. In one embodiment, the spectrometer 10 is configured so that the NMR measurements are conducted at 400 MHz for proton signals; in other embodiments the measurements may be carried out at 360 MHz or other suitable frequency. Other frequencies corresponding to a desired operational magnetic field strength may also be employed. Typically, a proton flow probe is installed, as is a temperature controller to maintain the sample temperature at 47+/−0.2 degrees C. Field homogeneity of the spectrometer 10 can be optimized by shimming on a sample of 99.8% $D_2O$ until the spectral linewidth of the HDO NMR signal is less than 0.6 Hz. The 90° RF excitation pulse width used for the $D_2O$ measurement is typically ca. 6-7 microseconds.

Referring again to FIG. 9, the spectrometer 10 is controlled by a digital computer 11 or other signal processing unit. The computer 11 should be capable of performing rapid Fourier transformations and may include for this purpose a hardwired sine table and hardwired multiply and divide circuit. It may also include a data link 12 to an external personal computer 13, and a direct-memory-access channel 14 which connects to a hard disc unit 15.

The digital computer 11 may also include a set of analog-to-digital converters, digital-to-analog converters and slow device I/O ports which connect through a pulse control and interface circuit 16 to the operating elements of the spectrometer. These elements include an RF transmitter 17 which produces an RF excitation pulse of the duration, frequency and magnitude directed by the digital computer 11, and an RF power amplifier 18 which amplifies the pulse and couples it to the RF transmit coil 19 that surrounds sample cell 20. The NMR signal produced by the excited sample in the presence of a 9.4 Tesla polarizing magnetic field produced by superconducting magnet 21 is received by a coil 22 and applied to an RF receiver 23. The amplified and filtered NMR signal is demodulated at 24 and the resulting quadrature signals are applied to the interface circuit 16 where they are digitized and input through the digital computer 11 to a file in the disc storage 15. The module 350 (FIG. 8) can be located in the digital computer 11 and/or in a secondary computer that may be on-site or remote. Additional automated clinical NMR analyzer systems suitable for analyzing biospecimen are described in co-pending, co-assigned U.S. patent application Ser. No. 11/093,596, the contents of which are hereby incorporated by reference as if recited in full herein.

After the NMR data are acquired from the sample in the measurement cell 20, processing by the computer 11 produces another file that can, as desired, be stored in the disc storage 15. This second file is a digital representation of the chemical shift spectrum and it is subsequently read out to the computer 13 for storage in its disc storage 25. Under the direction of a program stored in its memory, the computer 13, which may be personal, laptop, desktop, or other computer, processes the chemical shift spectrum in accordance with the teachings of the present invention to print a report, which is output to a printer 26 or electronically stored and relayed to a desired email address or URL. Those skilled in this art will recognize that other output devices, such as a computer display screen, may also be employed for the display of results.

It should be apparent to those skilled in the art that the functions performed by the computer 13 and its separate disc storage 25 may also be incorporated into the functions performed by the spectrometer's digital computer 11. In such case, the printer 26 may be connected directly to the digital computer 11. Other interfaces and output devices may also be employed, as are well-known to those skilled in this art.

The invention will now be described in more detail in the following non-limiting examples.

EXAMPLES

Exemplary weighting factors for LDL subclasses were calculated using data from two different studies with different coronary disease outcomes. Example 1 uses data on relations of large and small LDL particle numbers with carotid atherosclerosis as assessed on a per particle basis. Example 2 uses data on relations of IDL, large LDL, and small LDL particle numbers with incident CHD events (nonfatal myocardial infarction and CHD death) as assessed on a per particle basis.

Example 1

Shown in the table are the relations of large and small LDL particle numbers with carotid atherosclerosis as assessed on a per particle basis. TABLE 2 is an example of LDL subclass weights using data presented in Mora et al., *Both Large and Small LDL Particle Concentrations are Independently Associated with Carotid Atherosclerosis in the Multi-Ethnic Study of Atherosclerosis (MESA)*, Abstract presented at 2005 Scientific Sessions of the American Heart Association, Dallas, Tex., Circulation. 2005; 112: II-802.

TABLE 2

Exemplary LDL subclass weighting for Carotid Atherosclerosis

|  | Δ IMT (per 100 nmol/L) | LDL subclass weighting |
|---|---|---|
| Large LDL-P | 17.5 microns | 1.5 |
| Small LDL-P | 11.8 microns | 1.0 |

Data are from a linear regression model including both large and small LDL-P, adjusted for age, race, sex, hypertension, and smoking.

Shown in TABLE 2 are exemplary relations of large and small LDL particle numbers with carotid atherosclerosis as assessed on a per particle basis based on the MESA study. Subjects were 5,354 apparently healthy individuals enrolled in the Multi-Ethnic Study of Atherosclerosis (MESA) who were not taking lipid-lowering medication. Data show the change (increase) in carotid intima-media thickness (IMT) per 100 nmol/L increment in the concentration of large and small LDL-P. The ratio of Δ IMT for large LDL-P/small LDL-P is about 1.5, which gives a weighting factor for large LDL-P relative to small LDL-P.

It is contemplated that a third LDL subclass (IDL) can be included in the risk model and a different LDL subclass weighting can be used for the IDL contribution. IDL-P may have a weighting factor, which may be higher than the large LDL-P weight, such as between about 5-6 relative to small LDL-P.

Example 2

Shown in TABLE 3 are the relationships of IDL and large and small LDL particle numbers with incident CHD events (nonfatal myocardial infarction and CHD death) as assessed on a per particle basis. The data was derived from results presented in Otvos et al., *Low-Density Lipoprotein and High-Density Lipoprotein Particle Subclasses Predict Coronary Events and Are Favorably Changed by Gemfibrozil Therapy in the Veterans Affairs High-Density Lipoprotein Intervention Trial*, Circulation. 2006; 113; 1556-1563; originally published online Mar. 13, 2006.

TABLE 3

Exemplary LDL subclass weighting for incident CHD Events

|  | 1 SD | Odds Ratio (per 1 SD) | Beta coefficient (per 100 nmol/L) | LDL subclass weighting |
|---|---|---|---|---|
| IDL-P | 28 nmol/L | 1.13 | 0.436 | 5.7 |
| Large LDL-P | 250 nmol/L | 1.34 | 0.117 | 1.5 |
| Small LDL-P | 450 nmol/L | 1.41 | 0.076 | 1.0 |

Data are from a logistic regression model including LDL and HDL subclasses in the same model, adjusted for treatment group, age, hypertension, smoking, body mass index, and diabetes.

Subjects were men (364 cases, 697 controls) with existing coronary disease enrolled in the Veterans Affairs HDL Intervention Trial (VA-HIT). Data show the odds ratios for a new CHD event associated with a 1 SD increment in the on-trial concentration of each LDL subclass. The corresponding beta coefficients show the relationships of each subclass to CHD events on a per particle basis. The ratios of the beta coefficients for IDL-P and large LDL-P relative to small LDL-P give the weighting factors for IDL-P and large LDL-P relative to small LDL-P.

The beta coefficients can be calculated according to the mathematical expression:

beta coeff=ln OR/1 SD (100).

It is contemplated that additional studies may further optimize the weighting factors.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method of determining a subject's risk of having and/or developing coronary heart disease ("CHD"), comprising:
    obtaining concentration measurements of both small and large Low Density Lipoprotein (LDL) subclass particles in a blood plasma or serum sample of a subject; and
    programmatically adjusting at least one of the small and large LDL subclass particle measurements to increase or decrease at least one of the measurements; and
    determining the subject's risk of having and/or developing CHD based on both the small and large LDL subclass particle measurements, wherein at least one of the small and large LDL subclass measurements is the at least one adjusted LDL subclass particle measurement.

2. A method according to claim 1, wherein the measured large LDL subclass measurement is programmatically increased relative to the measured small LDL subclass measurement, the method further comprising electronically combining the increased large LDL subclass particle measurement and the small LDL subclass particle measurement to electronically automatically generate an LDL risk factor value, and wherein the determining step is based on the LDL risk factor value.

3. A method according to claim 2, wherein the obtaining step comprises obtaining the concentration of Intermediate Density Lipoprotein (IDL) particles, and wherein the adjusting step is carried out so that the IDL particle measurement and the large LDL subclass particle measurement are increased relative to the small LDL subclass particle measurement.

4. A method according to claim 1, wherein the adjusting step mathematically increases the measurement of the large LDL subclass particle measurement in units of concentration.

5. A method according to claim 4, wherein the adjusting step is based on a predetermined mathematical model that predicts a subject's cardiovascular risk, and wherein the mathematical model comprises a first weighting factor for the obtained concentration measurement of small LDL subclass particles and a second different weighting factor for the obtained concentration measurement of large LDL subclass particles.

6. A method according to claim 5, wherein the first and second weighting factors are multiplied to the respective small and large LDL subclass particle measurements and the results are added together to provide a weighted LDL particle risk factor number.

7. A method according to claim 1, wherein the adjusting step is carried out so that the large LDL subclass particle measurement is increased relative to the small LDL particle subclass concentration.

8. A method according to claim 1, wherein the obtaining step comprises substantially concurrently obtaining NMR derived concentration measurements of small and large LDL subclass particles.

9. A method of determining a subject's risk of having and/or developing CHD (coronary heart disease), comprising:
    measuring concentrations of small and large LDL (Low Density Lipoprotein) subclass particles in an in vitro blood plasma and/or serum sample of a subject; and
    programmatically adjusting at least one of the small or large LDL subclass particle concentration measurements by increasing or decreasing the at least one measurement based on a predetermined mathematical model, and determining the subject's LDL-based risk of CHD based on both the small and large LDL subclass particle measurements, wherein at least one of the small and large LDL subclass measurements is the at least one adjusted LDL subclass particle measurement.

10. A method according to claim 9, further comprising measuring concentration of Intermediate Density Lipoprotein (IDL) particles in the sample, and wherein the adjusting step is carried out to electronically adjust at least two of the small LDL subclass measurement, the large LDL subclass particle measurement and the IDL particle measurement and calculating an LDL risk number based on the adjusted particle measurements.

11. A method for determining a subject's risk of CHD coronary heart disease), comprising:
    obtaining NMR derived concentration measurements of small and large LDL (low density lipoprotein) subclass particles in a biosample of the subject;
    applying a weighting factor to at least one of the measured large and small LDL particle concentrations to increase or decrease one of the measured particle concentrations relative to the other; and
    calculating a LDL risk predictor number for the subject using both the small and large LDL particle concentrations, wherein at least one of the small and large LDL particle concentrations is the weighted LDL particle concentration(s).

12. A method according to claim 11, wherein the applying step comprises applying a weighting factor to the large LDL particle concentration, wherein the calculating step uses the weighted large LDL particle concentration summed with the small LDL particle concentration to generate the LDL risk predictor number for the subject.

13. A method according to claim 12, wherein the obtaining step comprises deconvolving at least one NMR spectroscopic signal of the biosample to calculate the small and large LDL particle subclass concentration measurements.

14. A method according to claim 13, wherein the obtaining step obtains a concentration measure of intermediate density lipoprotein (IDL) particles, and wherein the applying step is carried out to increase the IDL particle measurement and the large LDL particle measurement relative to the small LDL to obtain weighted large LDL and IDL particle measurements, subclass particle measurement and the calculating step uses the weighted large LDL and IDL particle measurements to generate the LDL risk predictor number.

15. A method according to claim 14, wherein the biosample is an in vitro blood plasma and/or serum sample, and wherein the applying step is carried out to increase the IDL particle measurement greater than the large LDL particle measurement and the calculating step uses the weighted large LDL and IDL particle measurements to generate the LDL risk predictor number.

16. A method according to claim 11, wherein the applying step is carried out to apply a first weight to the large LDL subclass concentration and a second weight relative to the small LDL subclass concentration with the first weight being greater than the second weight to calculate the LDL risk predictor number.

17. A computer program product for adjusting measured in vitro concentrations of LDL (low density lipoprotein) particles to assess CHD (coronary heart disease) risk, the computer program product comprising:
a computer readable storage medium having computer readable program code embodied in said medium, said computer-readable program code comprising:
computer readable program code that adjusts measured in vitro concentrations of at least one of small and large LDL (low density lipoprotein) particle subclasses to increase or decrease at least one of the small and large LDL particle subclass concentrations; and
computer readable program code that generates a LDL risk number using both the small and large LDL subclass particle concentrations and the adjusted concentration of at least one of the small and large LDL particle subclass concentrations to reflect a subject's risk of having or developing CHD.

18. A computer program product according to claim 17, further comprising computer readable program code that deconvolutes at least one NMR signal of a patient biosample into measured concentrations of small and large LDL particle subclasses.

19. A computer program product according to claim 17, wherein the computer readable program code that adjusts the measured concentrations is configured to increase the measured large LDL particle concentration relative to the small LDL particle concentration, and wherein the computer readable code that generates the LDL risk number uses the increased large LDL particle concentration to define the LDL risk number.

20. A computer program product according to claim 17, wherein the computer readable program code that adjusts at least one of the measured small and large LDL particle concentrations is configured to adjust at least two of small LDL particle concentration, large LDL particle concentration and intermediate density lipoprotein (IDL) particle concentration such that both the large LDL and IDL particle concentrations are increased relative to the small LDL subclass concentration, and wherein the computer readable code that generates the LDL risk number uses the at least two adjusted particle concentrations to generate the LDL risk number.

21. A computer program product according to claim 17, wherein the computer readable program code that generates the LDL risk number is configured to add the adjusted small and/or large LDL particle concentrations and scale the summation to thereby define a corresponding scalar LDL-based CHD risk.

22. A computer program product according to claim 17, wherein the computer readable program code that generates the LDL risk number combines the small and large LDL particle measurements, at least one of which being adjusted, and calculates a single LDL particle risk number in units of concentration.

23. A computer program product according to claim 17, wherein the computer readable program code that adjusts measured in vitro concentrations is configured to apply different weighting factors for small and large LDL particle concentrations, and wherein the computer readable code that generates the LDL risk number uses the weighted small and large LDL particle concentrations to predict CHD risk.

24. A computer program product according to claim 17, wherein the computer readable program code that adjusts measured in vitro concentrations is configured to increase the large LDL particle measurement relative to the small LDL particle measurement.

25. A computer program product according to claim 17, wherein the computer readable program code that adjusts the LDL particle concentrations is configured to multiply a first weighting factor for the concentration measurement of small LDL particles and multiply a second different weighting factor for the concentration measurement of large LDL particles, and wherein the computer readable program code that generates the LDL risk number sums the weighted small and large LDL particle concentrations.

26. A computer program product according to claim 25, wherein the computer readable program code that generates the LDL risk number is configured to scale the sum of the multiplied small and large LDL particle concentration measurements to provide a scalar weighted LDL particle risk number.

27. A computer program product according to claim 26, wherein the computer readable program code that generates the LDL risk number is configured to increase the large LDL particle concentration measurement relative to the small LDL particle concentration measurement.

28. An apparatus for obtaining data regarding lipoprotein constituents in a subject, comprising:
an NMR spectrometer for acquiring at least one NMR spectrum of an in vitro blood plasma or serum sample of a subject; and
at least one processor in communication with the NMR spectrometer, the at least one processor configured to (a) determine concentrations of small and large LDL (low density lipoprotein) particle subclasses in the sample from the subject, (b)
increase or decrease at least one of the determined small and large LDL particle concentrations to provide at least one adjusted concentration value, and (c) determine the subect's risk of developing or having CHD (coronary heart disease) based on both the small and large LDL subclass measurements, wherein at least one of the small and large LDL subclass measurements is the at least one adjusted concentration value.

29. An apparatus according to claim 28, wherein the at least one NMR spectrum is a composite spectrum, the at least one processor further configured to define a plurality of individual NMR constituent spectra, each associated with a selected reference lipoprotein constituent signal lineshape, each constituent spectrum having associated spectra that contribute to the composite NMR spectrum of the blood plasma or serum sample.

30. An apparatus according to claim 28, wherein the processor is configured to increase the measured large LDL particle concentration using a defined multiplier relative to the small LDL particle concentration to generate the adjusted concentration value.

31. An apparatus according to claim 30, wherein the processor is configured to generate an LDL risk number using adjusted small and large LDL particle concentrations, wherein the processor is configured to multiply a first weighting factor to the small LDL particle concentration and a second different weighting factor to the large LDL particle concentration, and wherein the second weighting factor is larger than the first weighting factor.

32. An apparatus according to claim 28, wherein the at least one processor is configured to determine a concentration of IDL (intermediate density lipoprotein) particles in the sample and increase the IDL concentration as well as the concentration of large LDL particles relative to the small LDL particle concentration and wherein the at least one processor is configured to determine the subect's CHD risk using the increased IDL and large LDL particle concentrations.

33. An apparatus according to claim 32, wherein the at least one processor is configured to determine an LDL risk number using the increased LDL and IDL particle concentrations to determine the subject's CHD risk.

34. A method of calculating an LDL risk parameter number used to assess a person's risk of having or developing CHD (coronary heart disease) comprising:
  calculating a LDL risk parameter number for a person by adding together adjusted concentrations of at least two of small low density lipoprotein (LDL), large LDL and IDL (intermediate density lipoprotein) particle measured concentrations whereby the adjusted concentrations are increased or decreased relative to the measured particle concentrations, wherein at least one of the adjusted large LDL or IDL particle concentrations is increased relative to the measured small LDL particle concentration, wherein the LDL risk parameter number defines the person's risk of having or developing CHD, and wherein increased risk is associated with greater values of the LDL risk parameter number.

35. A method according to claim 34, further comprising electronically defining a risk of developing or having CHD associated with the LDL risk parameter number.

36. A method according to claim 34, further comprising mathematically scaling the calculated LDL risk parameter number to thereby provide a scalar risk number that defines the CHD risk.

37. A method according to claim 34, wherein both the measured IDL and large LDL particle concentrations are increased relative to the measured small LDL particle concentration to provide the adjusted concentrations and, wherein the adjusted IDL and LDL particle concentrations are added to the small LDL particle concentration to generate the LDL risk parameter number.

38. A method according to claim 37, wherein the IDL particle concentration is increased more than the large LDL particle concentration to provide the adjusted concentrations.

* * * * *

UNITED STATES PATENT AND TRADEMARK OFFICE
CERTIFICATE OF CORRECTION

PATENT NO. : 7,790,465 B2
APPLICATION NO. : 11/379275
DATED : September 7, 2010
INVENTOR(S) : Otvos Page 1 of 2

It is certified that error appears in the above-identified patent and that said Letters Patent is hereby corrected as shown below:

In the Specification:
Column 3, Line 67: Please correct "example, mmol/L"
to read -- example, nmol/L --

Column 17, Line 61, Matrix (9): Please correct $$[W] = \begin{bmatrix} w_1 & 0 & \cdots & 0 \\ 0 & w_2 & \cdots & 0 \\ \vdots & \vdots & \ddots & \vdots \\ 0 & 0 & \cdots & w_m \end{bmatrix} \quad (9)$$

to read $$[W] = \begin{bmatrix} w_1 & 0 & \cdots & 0 \\ 0 & w_2 & \cdots & 0 \\ \vdots & \vdots & \ddots & \vdots \\ 0 & 0 & \cdots & w_m \end{bmatrix} \quad (9)$$

Column 18, Line 6, Matrix (11): Please correct $$[W]^{-1} = \begin{bmatrix} 1/w_1 & 0 & \cdots & 0 \\ 0 & 1/w_2 & \cdots & 0 \\ \vdots & \vdots & \ddots & \vdots \\ 0 & 0 & \cdots & 1/w_m \end{bmatrix} \quad (11)$$

Signed and Sealed this
First Day of March, 2011

David J. Kappos
*Director of the United States Patent and Trademark Office* to read $$[W]^{-1} = \begin{bmatrix} 1/w_1 & 0 & \cdots & 0 \\ 0 & 1/w_2 & \cdots & 0 \\ \vdots & \vdots & \ddots & \vdots \\ 0 & 0 & \cdots & 1/w_m \end{bmatrix} \quad (11)$$

Column 24, Line 12, Equation (17): Please correct "$M = QAQ^T$"

to read -- $M = Q\Lambda Q^T$ --

Line 13: Please correct "whereQ(k+w)"
to read -- where $Q$ ($k+w$) --

Line 21: Please correct "A($\lambda$): $\Lambda$" to read -- A($\lambda$): $\mathcal{R}$ --

Column 24, Line 25, Equation 18: Please correct "$\Lambda = \Lambda_{red}$" to read -- $\Lambda_{red}$ --

Line 45, Equation 21: Please correct

"$b = Q\Lambda_{red}^{-1} Q^T X^T Y$"

to read -- $b = Q\Lambda_{red}^{-1} Q^T X^T Y$ --

In the Claims:
Column 28, Claim 11, Line 42: Please correct "coronary heart disease)"
               to read -- (coronary heart disease) --

Column 29, Claim 14, Lines 2,3,4: Please correct "to obtain weighted large LDL
               and IDL particle measurements, subclass particle measurement"
               to read -- subclass particle measurement to obtain weighted large LDL and IDL
               particle measurements, --